US012533132B2

(12) United States Patent
Perkins et al.

(10) Patent No.: US 12,533,132 B2
(45) Date of Patent: Jan. 27, 2026

(54) DEVICE FOR SPREADING TOPICAL SKIN ADHESIVE

(71) Applicant: Cilag GmbH International, Zug (CH)

(72) Inventors: Jason T. Perkins, Easton, PA (US); Grant S. Miller, Flanders, NJ (US); Douglas E. Souls, Andover, NJ (US); Robert A. Rousseau, Riegelsville, PA (US)

(73) Assignee: Cilag GmbH International, Zug (CH)

( * ) Notice: Subject to any disclaimer, the term of this patent is extended or adjusted under 35 U.S.C. 154(b) by 167 days.

(21) Appl. No.: 18/490,875

(22) Filed: Oct. 20, 2023

(65) Prior Publication Data

US 2024/0164778 A1 May 23, 2024

Related U.S. Application Data

(60) Provisional application No. 63/427,132, filed on Nov. 22, 2022.

(51) Int. Cl.
*A61B 17/08* (2006.01)

(52) U.S. Cl.
CPC .................................. *A61B 17/085* (2013.01)

(58) Field of Classification Search
CPC .......... A61B 17/00491; A61B 17/0057; A61B 17/085; A61B 2017/00495;
(Continued)

(56) References Cited

U.S. PATENT DOCUMENTS 5,749,117 A * 5/1998 Forsline .................... B44D 3/00 401/199
6,325,565 B1 12/2001 Girardot et al.
(Continued)

FOREIGN PATENT DOCUMENTS

| | | |
|---|---|---|
| DE | 29501724 U1 | 3/1995 |
| GB | 2076865 | 12/1998 |
| IT | 20110140 A1 | 4/2013 |

OTHER PUBLICATIONS

Design U.S. Appl. No. 29/860,717, filed Nov. 22, 2022, by Perkins et al., entitled: "Device for Spreading Topical Skin Adhesive."
(Continued)

*Primary Examiner* — Robert A Lynch
(74) *Attorney, Agent, or Firm* — Amir Bisbara

(57) ABSTRACT

An apparatus includes a proximal body portion configured to be gripped by a user, a distal body portion that terminates at a spreading tip configured to spread a topical skin adhesive along an application surface, and a flexural body portion that interconnects the proximal and distal body portions to define a monolithic body. In response to an input force applied by a user to the proximal body portion when the spreading tip is positioned against the application surface, the flexural body portion is configured to buckle non-uniformly along a lateral width of the apparatus. Additionally, or alternatively, the flexural body portion is configured to elastically deform so that the distal body portion angularly deflects relative to the proximal body portion to thereby limit to a predetermined range a resultant normal force exerted by the spreading tip on the topical skin adhesive along the application surface.

18 Claims, 18 Drawing Sheets

(58) Field of Classification Search
CPC ........... A61B 2017/00659; A61B 2017/00951; A61M 35/003; A61F 13/023; A61H 11/00; A61H 7/003; A61H 2201/1253; A45D 37/00; A45D 40/26; A45D 40/28; A45D 2200/10; A45D 2200/1018; A45D 2200/1027; B05C 17/00; B05C 17/10
See application file for complete search history.

(56) References Cited

U.S. PATENT DOCUMENTS

| | | | | |
|---|---|---|---|---|
| 8,097,008 | B2 | 1/2012 | Henderson | |
| 10,610,035 | B2 | 4/2020 | McIver et al. | |
| 11,479,669 | B2 | 10/2022 | Ou | |
| 11,518,604 | B2 | 12/2022 | Ou et al. | |
| 11,589,867 | B2 | 2/2023 | Ou et al. | |
| 11,712,229 | B2 | 8/2023 | Ou et al. | |
| 2006/0245819 | A1 | 11/2006 | Owens | |
| 2018/0000222 | A1* | 1/2018 | Caulier | A45D 33/36 |
| 2018/0085260 | A1 | 3/2018 | Quintero | |
| 2019/0261762 | A1 | 8/2019 | Chaillet-Piquand et al. | |
| 2020/0390534 | A1* | 12/2020 | Curtis | A46B 9/02 |
| 2021/0369258 | A1* | 12/2021 | Ou | A61B 17/00491 |
| 2021/0369639 | A1 | 12/2021 | Ou | |
| 2022/0062089 | A1 | 3/2022 | Martinez Millet | |
| 2022/0395643 | A1 | 12/2022 | Ou et al. | |

OTHER PUBLICATIONS

U.S. Appl. No. 17/991,945, filed Nov. 22, 2022, by Quintero et al., entitled: "Surgical Mesh Securing Device for Wound Closure System."

U.S. Appl. No. 17/991,950, filed Nov. 22, 2022, by Quintero et al., entitled: "Wound Closure System Having Microcannulaic Pathways."

U.S. Appl. No. 17/991,992, filed Nov. 22, 2022, by Ou et al., entitled: "Application of Topical Skin Adhesive to Surgical Mesh."

U.S. Appl. No. 63/427,132, filed Nov. 22, 2022, by Perkins et al., entitled: "Device for Spreading Topical Skin Adhesive."

International Search Report and Written Opinion dated Feb. 22, 2024, for International Application No. PCT/IB2023/061727, 23 pages.

* cited by examiner

DEVICE FOR SPREADING TOPICAL SKIN ADHESIVE

PRIORITY

This application claims the benefit of U.S. Provisional Pat. App. No. 63/427,132, entitled "Device for Spreading Topical Skin Adhesive," filed Nov. 22, 2022, the disclosure of which is incorporated by reference herein in its entirety.

BACKGROUND

A wound closure system (also referred to as a skin closure system) may be used at the conclusion of a surgical procedure on a patient to close a wound (e.g., a surgical incision) that was formed in the patient's skin for accessing a target anatomical structure. By way of example, wound closure systems may include components such as sutures, substrates, and/or liquid topical skin adhesives that are applied by a surgeon to approximate the edges of the wound and, in some cases, form a stable and protective layer over the wound that promotes efficient healing. In some instances, one or more components of the applied wound closure system may be absorbed by the patient during the healing process. Following healing of the wound, remaining components of the wound closure system may be removed from the skin by a surgeon, and/or they may automatically separate from the skin such that they may be discarded by the patient.

While various wound closure systems and associated components and methods have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the description given below, serve to explain the principles of the present invention.

Figure 1:
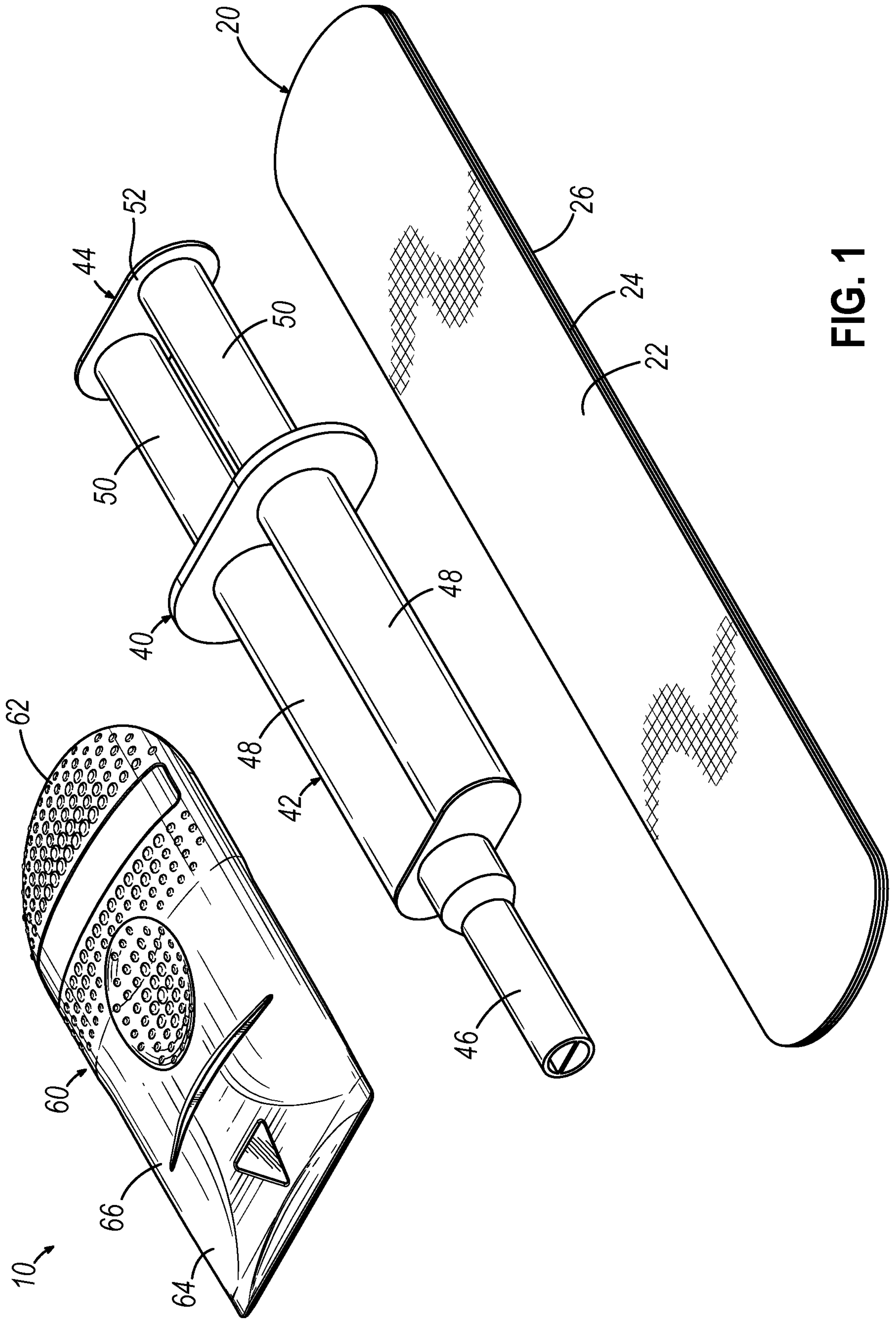
FIG. 1 depicts a perspective view of an example of a wound closure system that includes a wound closure device, an adhesive applicator, and an adhesive spreader.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "side," "upwardly," and "downwardly" also are used herein for reference to relative positions and directions. Such terms are used below with reference to views as illustrated for clarity and are not intended to limit the invention described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. WOUND CLOSURE SYSTEM

FIG. 1 shows an example of a wound closure system (10) that includes a wound closure device (20) (also referred to as a patch) configured to be applied to a patient's wound (W), an adhesive applicator (40) configured to apply a topical skin adhesive (54) (see FIG. 3D) to the applied wound closure device (20), and an adhesive spreader (60) configured to spread the applied topical skin adhesive (54) onto and through wound closure device (20). Each of these components is described in greater detail below.

Figure 2:
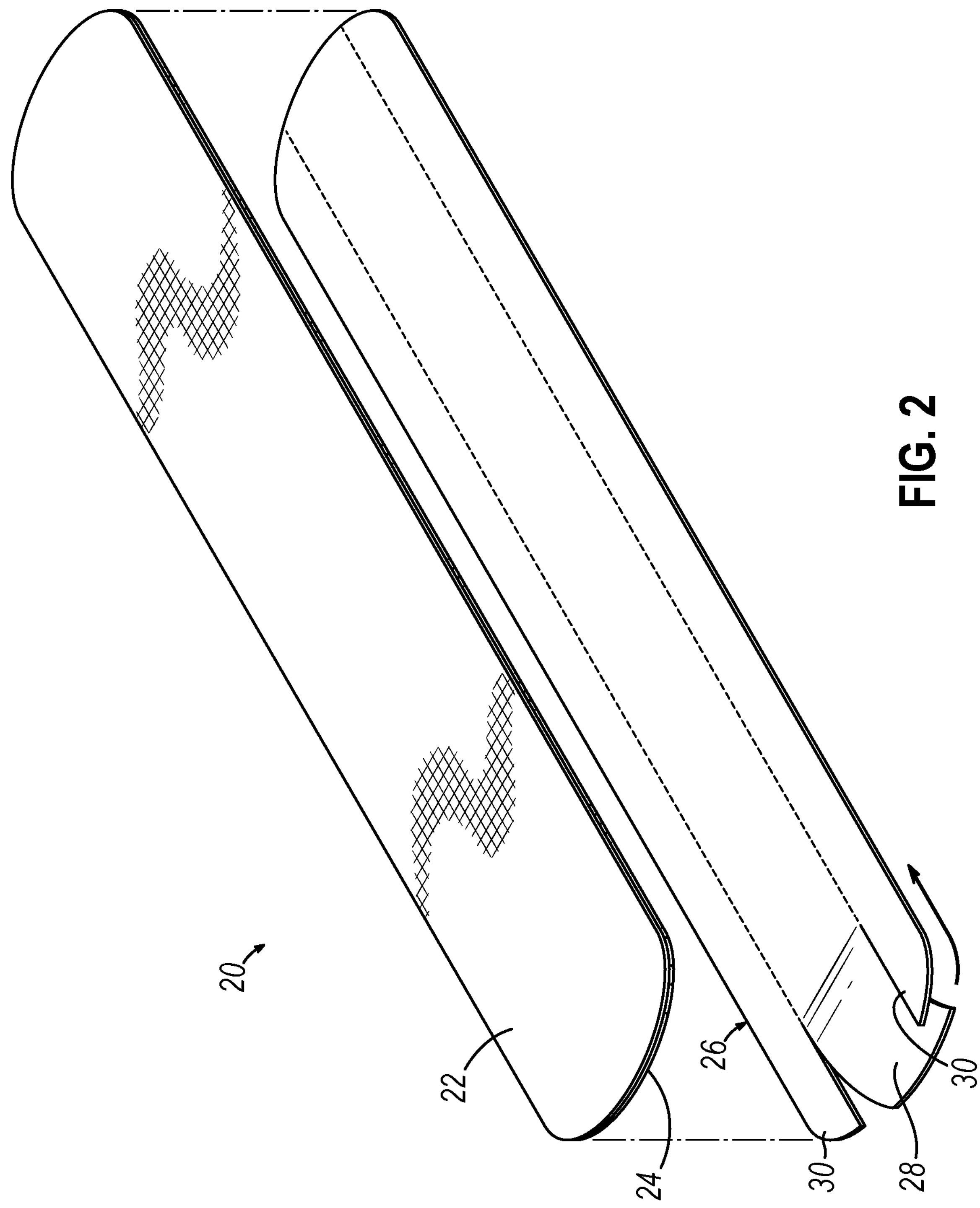
FIG. 2 depicts a disassembled perspective view of the wound closure device of FIG. 1, showing a mesh layer, a pressure sensitive adhesive layer, and a removable backing layer.

As shown best in FIG. 2, wound closure device (20) of the present version has an elongate, generally rectangular shape and a triple layer construction. More specifically, wound closure device (20) includes a layer of substrate in the form of a textile mesh (22), a layer of pressure sensitive adhesive (24) formed as a continuous or non-continuous coating along the lower skin-facing side of mesh (22), and a layer of backing (26) removably applied to the lower side of pressure sensitive adhesive (24). It will be understood that the term "wound closure device" as used herein encompasses wound closure device (20) both with and without backing (26), which may be removed and discarded during application of wound closure device (20) to a patient, as described in greater detail below.

Mesh (22) is configured to retain a liquid topical skin adhesive and may be formed of polyethylene (PET) or any other suitable surgical textile material. Pressure sensitive adhesive (24) is configured to enable wound closure device (20) to self-adhere to a patient's skin in response to a pressure being applied to the upper side of mesh (22) during its application by a surgeon. Backing (26) serves to protect pressure sensitive adhesive (24) before application of wound closure device (20) to the patient. In the present version, backing (26) includes elongate arrays of perforations that extend longitudinally and define an elongate central backing section (28) and a pair of elongate side backing sections (30). Though each backing section (28, 30) is shown as generally rectangular in the present version, backing sections (28, 30) may be of various alternative shapes, sizes, and quantities in other versions.

As shown in FIG. 1, adhesive applicator (40) includes an applicator body (42), a plunger unit (44) slidably received within an open proximal end of applicator body (42), and a static mixer (46) secured to a distal end of applicator body (42). Applicator body (42) includes a pair of barrels (48) arranged side by side, where each barrel (48) houses a respective part of a two-part liquid topical skin adhesive. Plunger unit (44) includes a pair of plungers (50) that are arranged side by side and are interconnected at their proximal ends by a bridge (52). Each plunger (50) is actuatable distally through a respective barrel (48) of applicator body (42) to force the corresponding liquid adhesive part distally into static mixer (46). Static mixer (46) is configured to receive the first and second adhesive parts and direct them around and through a series of static baffles and passages (not shown) that mix the two adhesive parts together into a homogenous liquid adhesive (54) that is then dispensed through an open distal end of static mixer (46), as shown in FIG. 3D described below.

In the present version, liquid topical skin adhesive (54) is in the form of a silicone-based topical skin adhesive that is configured to cure on skin at body temperature in less than two minutes. Once cured, topical skin adhesive (54) remains elastomeric such that a given section of cured adhesive (54) is configured to stretch up to 160% of its cured length and then fully recover to the cured length. Accordingly, wound closure system (10) may be particularly effective for use on actuatable body parts of a patient such as a knee, wrist, elbow, or other joint, for example.

As also shown in FIG. 1, adhesive spreader (60) of the present version has a monolithic body that includes a proximal body portion (62) configured to be gripped by a user, a distal body portion (64) that terminates at a tip configured to spread applied topical skin adhesive (54), and an intermediate flexural body portion (66) that interconnects the proximal and distal body portions (62, 64). Flexural body portion (66) is configured to elastically deform so that distal body portion (64) angularly deflects relative to proximal body portion (62) to promote effective spreading of topical skin adhesive (54) along wound closure device (20) with a suitable normal force within a predetermined range, as described in greater detail below.

FIGS. 3A-3D show an example of wound closure system (10) being used to close a wound (W) formed in the skin (S) of a patient. In some procedures, wound (W) may be at least partially closed with one or more sutures, for example at deeper portions of wound (W), prior to use of wound closure system (10). Additionally, before wound closure device (20) is applied to the patient, it may be trimmed by a surgeon to any suitable shape as desired.

Figure 3A:
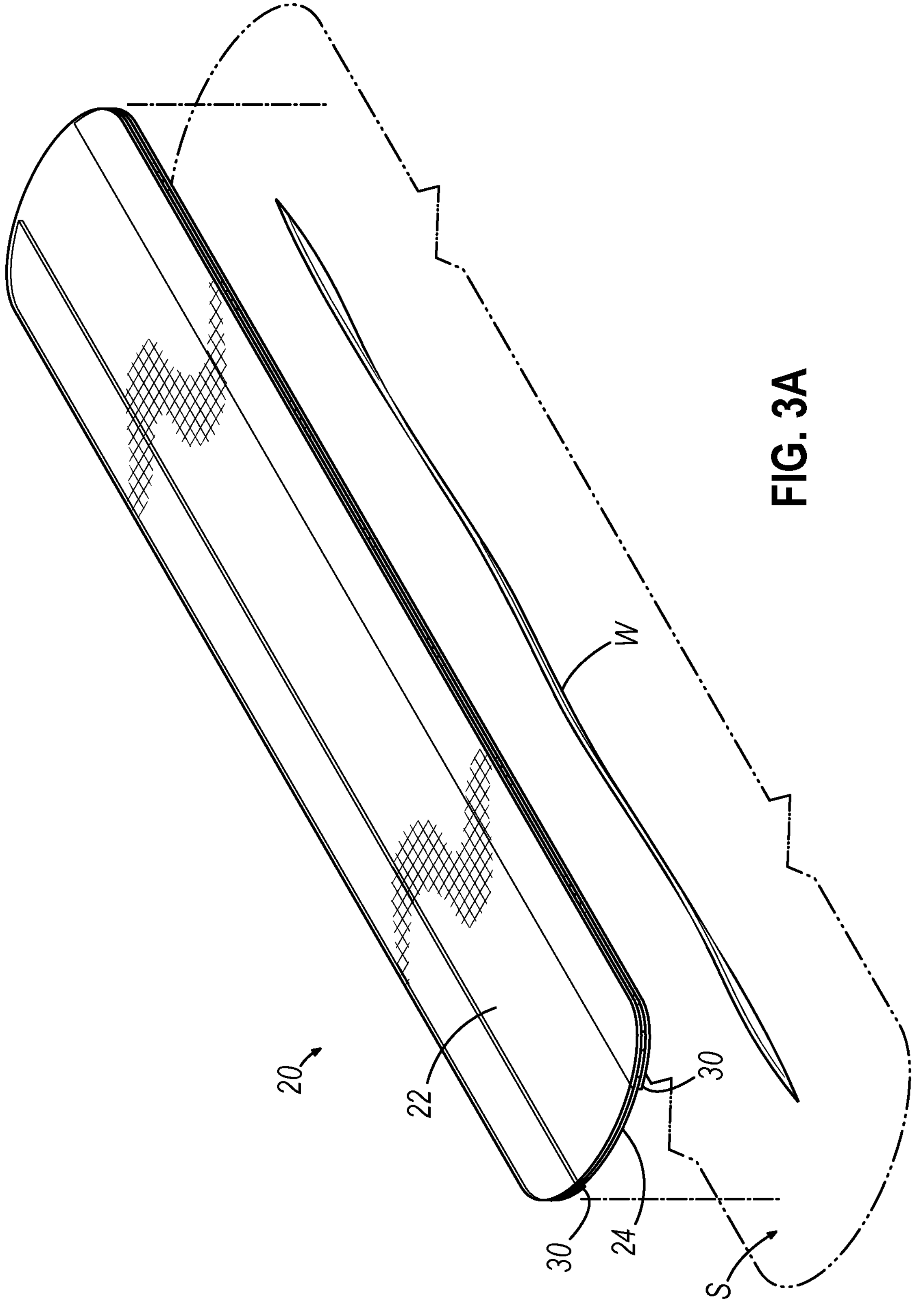
FIG. 3A depicts a perspective view of the wound closure device of FIG. 1 aligned longitudinally with a wound in the skin of a patient, showing a central section of the backing layer having been removed.
Figure 3B:
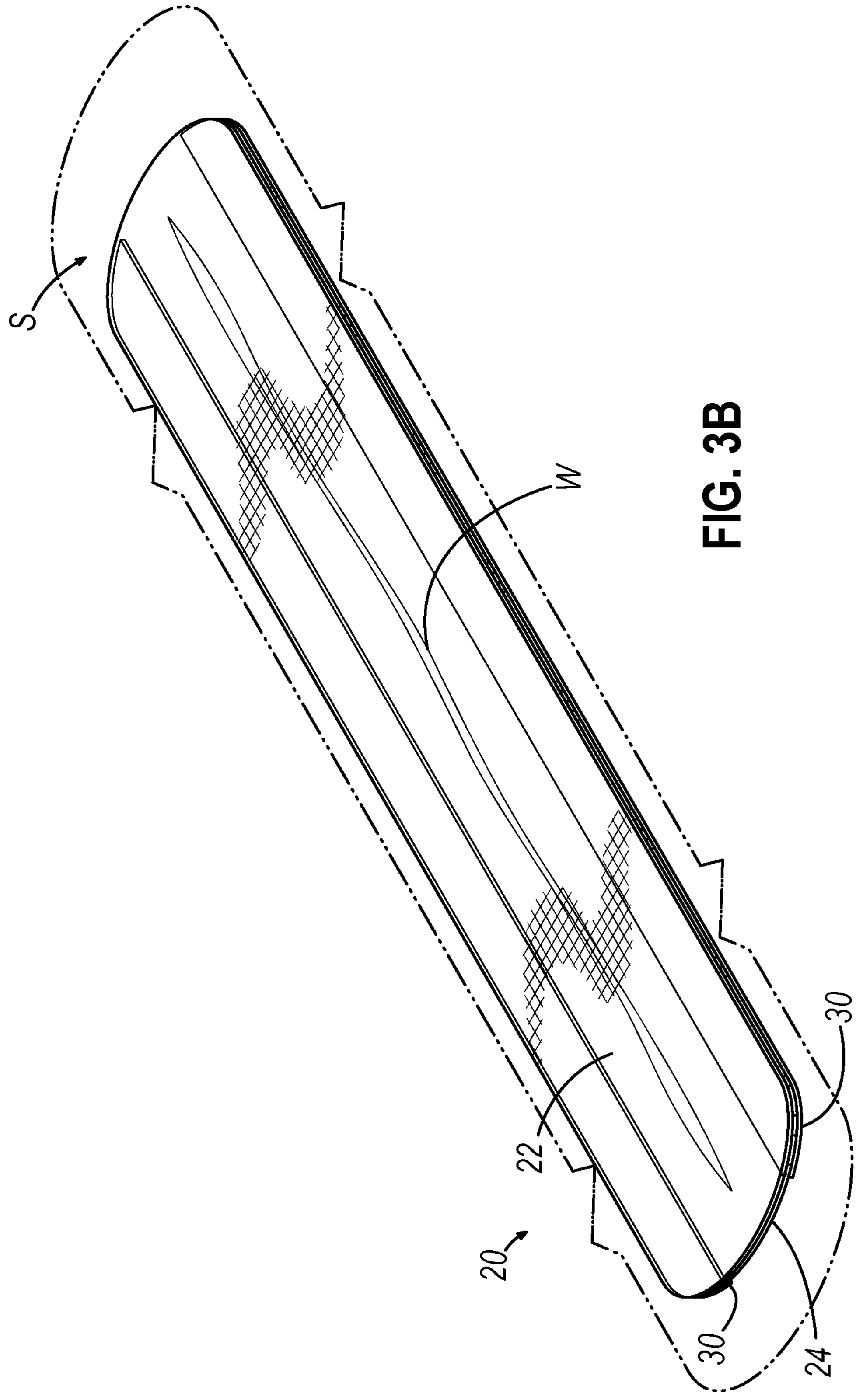
FIG. 3B depicts a perspective view of the wound closure device of FIG. 1 applied to the patient's skin over the wound to approximate the edges of the wound.
Figure 3C:
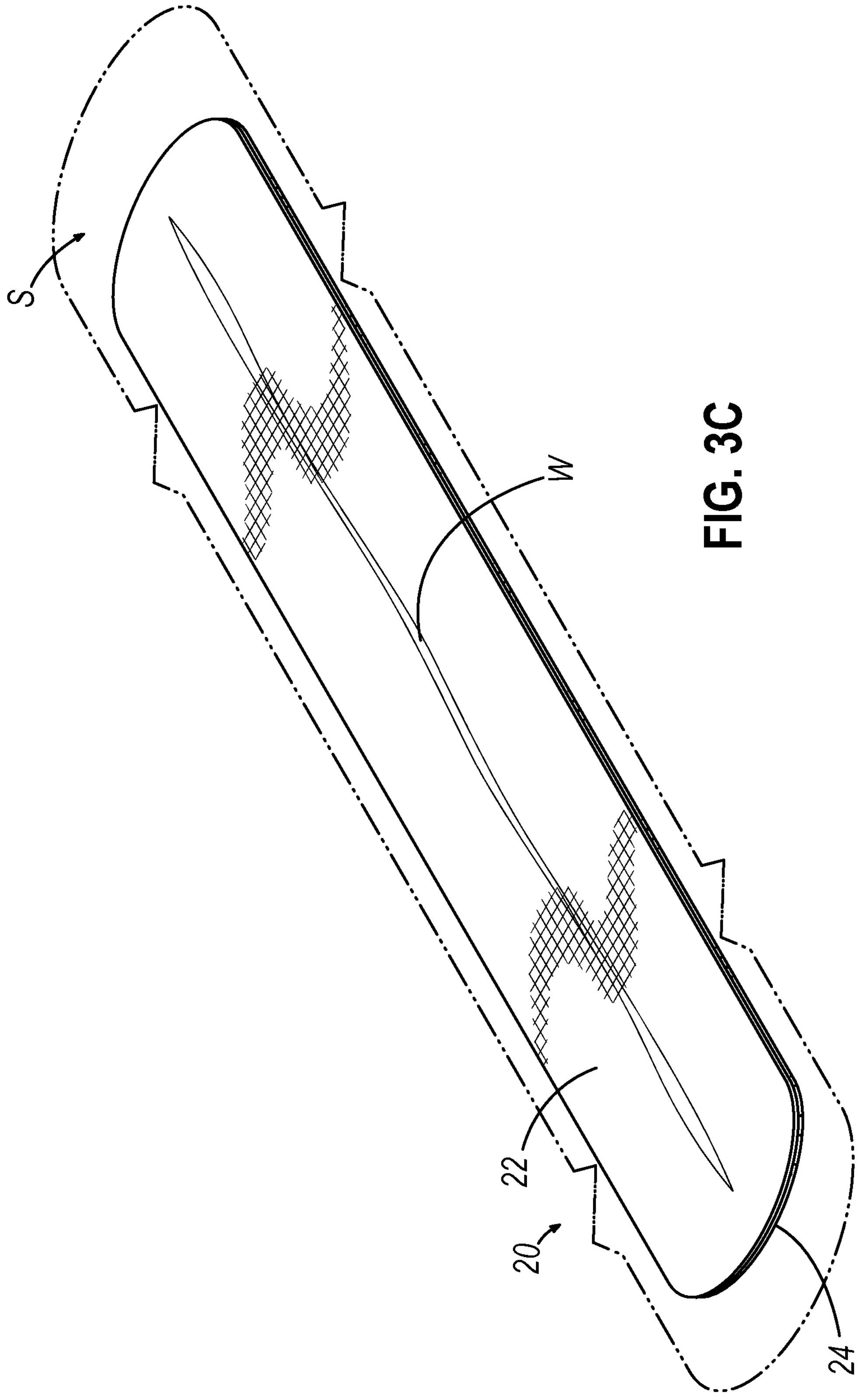
FIG. 3C depicts a perspective view of the wound closure device of FIG. 1 applied to the patient's skin over the wound, showing remaining sections of the backing layer having been removed so the wound closure device is fully adhered to the skin.
Figure 3D:
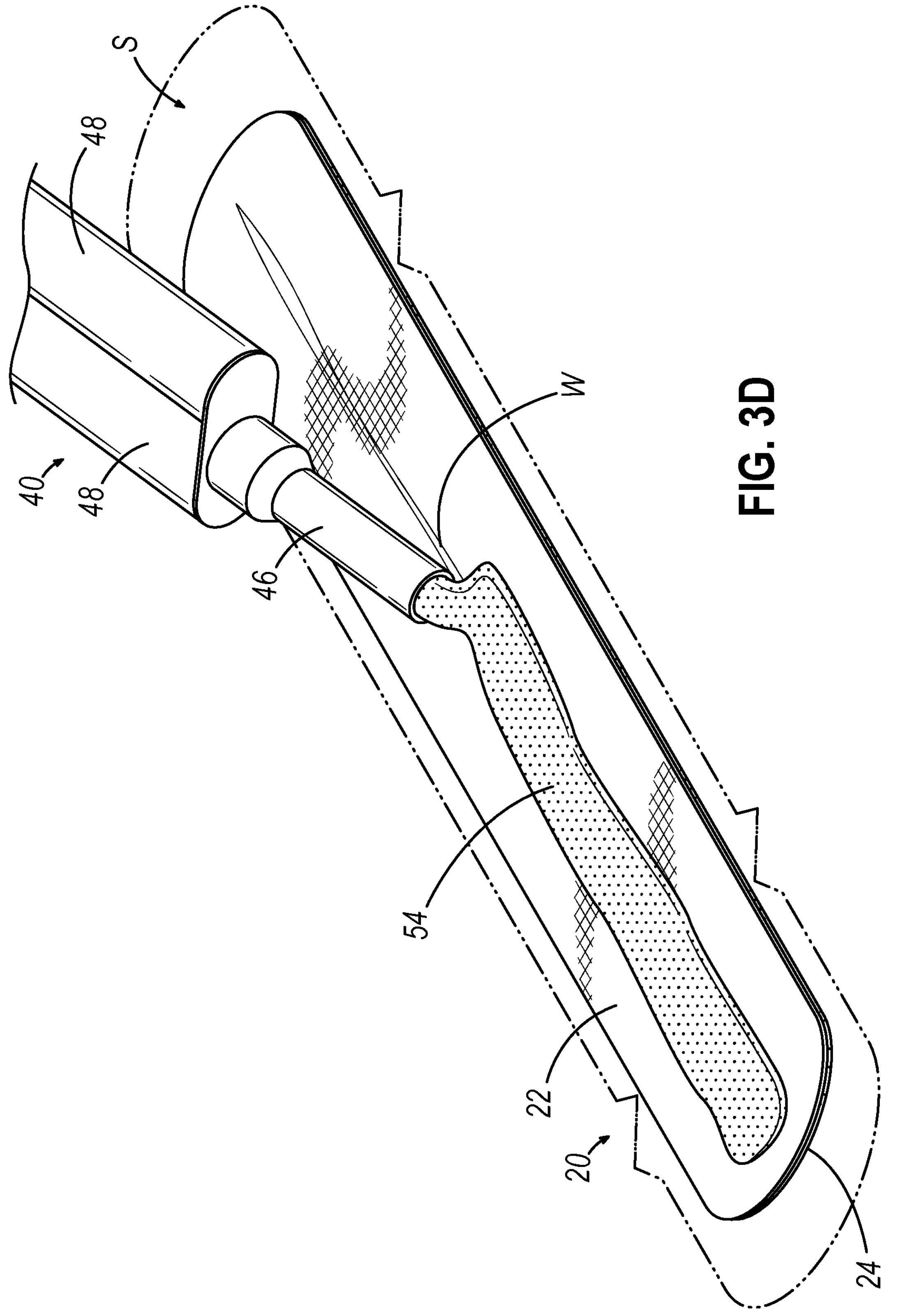
FIG. 3D depicts a perspective view of the wound closure device of FIG. 1 applied to the patient's skin over the wound, showing application of a liquid topical skin adhesive onto the mesh layer with the adhesive applicator.

As shown in FIG. 3A, central backing section (28) is removed from wound closure device (20) to expose a central window of mesh (22) and pressure sensitive adhesive (24), and an imaginary centerline of wound closure device (20) is aligned longitudinally with the edges of wound (W). Wound closure device (20) is then applied to the patient skin (S) over wound (W) and the surgeon applies pressure to the central portion of mesh (22) to force pressure sensitive adhesive (24) to adhere to the skin (S), thus fixing the edges of wound (W) relative to one another. Before this step, the edges of wound (W) may be held in an approximated state by the surgeon. Alternatively, during this step the central portion of wound closure device (20) may be applied in a laterally alternating manner to approximate the edges of wound (W) during application. With either approach, wound closure device (20) is configured to hold the edges of wound (W) in an approximated state following this initial step of application. Once the surgeon is satisfied with the position of wound closure device (20) relative to wound (W), the surgeon may then remove the remaining two side backing sections (30) to adhere the reminder of wound closure device (20) to skin (S).

As shown in FIG. 3D, adhesive applicator (40) is then used to apply a pattern of topical skin adhesive (54) to the upper side of mesh (22) of the applied wound closure device (20). While adhesive applicator (40) is shown applying a linear bead of topical skin adhesive (54) in the present version, it will be appreciated that various other patterns of topical skin adhesive (54) may be applied in other versions, such as a T-shaped pattern or a wave-shaped pattern as disclosed in U.S. patent application Ser. No. 17/991,992, entitled "Application of Topical Skin Adhesive to Surgical Mesh," filed Nov. 22, 2022, published as U.S. Pub. No. 2024/0165292 on May 23, 2024, the disclosure of which is incorporated by reference herein, in its entirety.

Figure 3E:
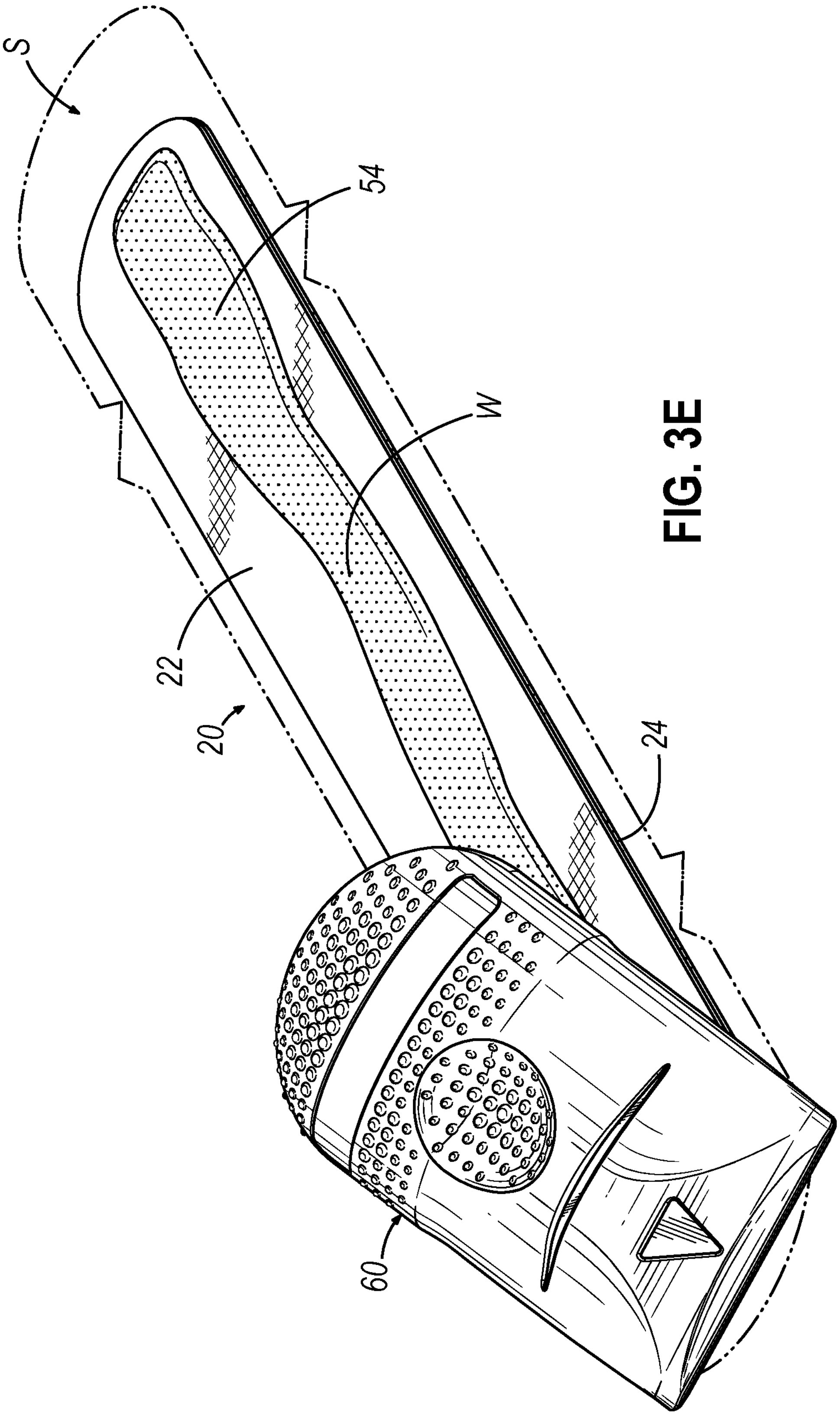
FIG. 3E depicts a perspective view of the wound closure device of FIG. 1 applied to the patient's skin over the wound, showing the adhesive spreader positioned against the patient at the start of an adhesive spreading stroke for spreading the applied topical skin adhesive over and through the wound closure device.
Figure 3F:
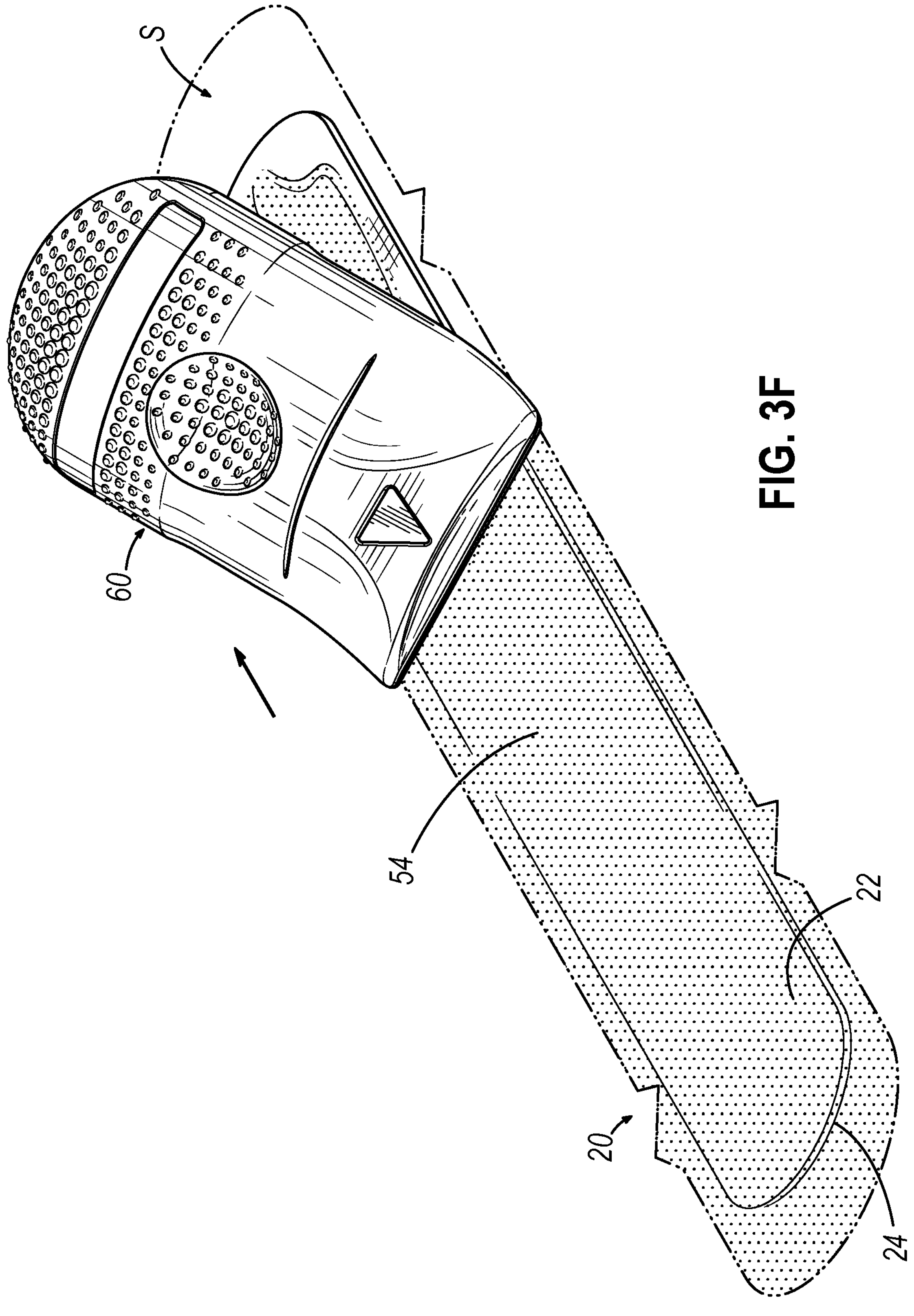
FIG. 3F depicts a perspective view of the wound closure device of FIG. 1 applied to the patient's skin over the wound, showing the adhesive spreader during a subsequent portion of the adhesive spreading stroke.

As shown in FIGS. 3E-3F, adhesive spreader (60) is then used to spread the applied topical skin adhesive (54) uniformly over wound closure device (20) to force the topical skin adhesive (54) through the layers of mesh (22) and pressure sensitive adhesive (24) and directly against wound (W) and the surrounding skin (S). In that regard, the layers of mesh (22) and pressure sensitive adhesive (24) may be at least partially permeable to permit forced passage of topical skin adhesive (54) therethrough. As shown in FIG. 3E, flexural body portion (66) of adhesive spreader (60) may be in a non-deformed state when adhesive spreader (60) is first positioned against wound closure device (20) at the beginning of an adhesive spreading stroke. As adhesive spreader (60) is dragged longitudinally along wound closure device (20), the input force exerted by the user may cause flexural body portion (66) to elastically deform such that distal body portion (64) angularly deflects relative to proximal body portion (62), as shown in FIG. 3F. The degree of deformation of flexural body portion (66) may be directly related to the viscosity of topical skin adhesive (54). In particular, a greater viscosity may require that the user exert a greater input force through proximal body portion (62) to effectively spread topical skin adhesive (54) over and through wound closure device (20), such that the flexural body portion (66) deforms a relatively greater amount. Conversely, a lesser viscosity may require a lesser input force such that the flexural body portion (66) deforms less or not at all.

Optionally, topical skin adhesive (54) may also be spread over adjacent portions of skin (S) not covered by wound closure device (20) to ensure that an entirety of mesh (22) is embedded with topical skin adhesive (54). For instance, and by way of example only, topical skin adhesive (54) may be spread onto at least 1 cm of skin (S) about the entire outer perimeter of the applied wound closure device (20). Once topical skin adhesive (54) has been fully spread over wound closure device (20), any topical skin adhesive (54) on skin (S) beyond the perimeter of device (20) may then be wiped away with sterile gauze, for example. Additionally, in some instances, a quantity of topical skin adhesive (54) may be applied between the edges of wound (W) before wound closure device (20) is applied to the skin (S). The applied topical skin adhesive (54) then cures within and over wound closure device (20) to form a composite microbial barrier over wound (W) that maintains a protective environment that promotes efficient healing. Following healing of wound (W), wound closure device (20) may be removed from the skin (S) manually (e.g., by a surgeon) or it may automatically separate from the skin (S) such that it may be discarded by the patient.

Wound closure system (10) may be further configured and operable in accordance with at least some of the teachings of U.S. Pat. No. 11,712,229, entitled "Systems, Devices and Methods for Dispensing and Curing Silicone Based Topical Skin Adhesives," issued Aug. 1, 2023, the disclosure of which is incorporated by reference herein, in its entirety; U.S. Pat. No. 11,518,604, entitled "Systems, Methods and Devices for Aerosol Spraying of Silicone Based Topical Skin Adhesives for Sealing Wounds," issued Dec. 6, 2022, the disclosure of which is incorporated by reference herein, in its entirety; U.S. Pat. No. 11,479,669, entitled "Novel Topical Skin Closure Compositions and Systems," issued Oct. 25, 2022, the disclosure of which is incorporated by reference herein, in its entirety; U.S. Pat. Pub. No. 2021/0369639, entitled "Novel Antimicrobial Topical Skin Closure Compositions and Systems," published Dec. 2, 2021, the disclosure of which is incorporated by reference herein, in its entirety; U.S. Pat. No. 11,589,867, entitled "Anisotropic Wound Closure Systems," issued Feb. 28, 2023, the disclosure of which is incorporated by reference herein, in its entirety; and/or U.S. Pat. Pub. No. 2022/0395643, entitled "Gas Sterilizable Syringes Having Apertures Covered by Gas Permeable Barriers for Enabling Ingress and Egress of Sterilization Gases While Preventing Leakage of Flowable Materials," published Dec. 15, 2022, the disclosure of which is incorporated by reference herein, in its entirety.

II. ADHESIVE SPREADER

As indicated above, adhesive spreader (60) of the present version has a monolithic body defined by proximal body portion (62), distal body portion (64), and flexural body portion (66) in combination. As described in greater detail below, this monolithic body has a variable buckling strength along its lateral width and is configured to elastically deform at flexural body portion (66) and at its distal end to ensure consistent application of a normal force of a predetermined, appropriate range to topical skin adhesive (54) and wound closure device (20) during use. In that regard, adhesive spreader (60) is configured to ensure that a topical skin adhesive, such as topical skin adhesive (54), is driven sufficiently through wound closure device (20) to contact and bond with skin (S) without transmitting excessive normal force that could dislodge wound closure device (20) from skin (S).

Figure 4:
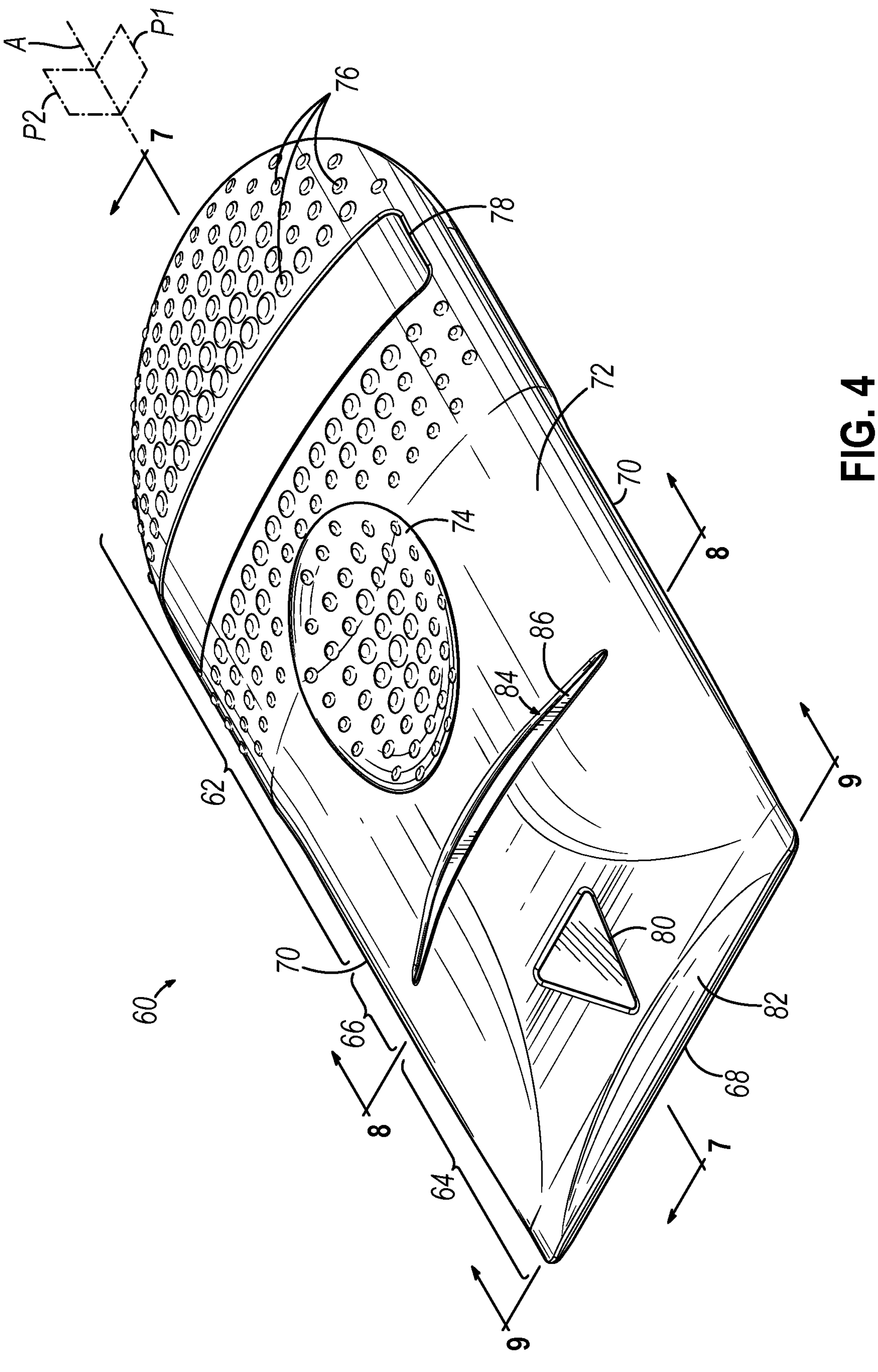
FIG. 4 depicts a perspective view of the adhesive spreader of FIG. 1.

As shown in FIG. 4, the monolithic body of adhesive spreader (60) extends longitudinally between a rounded proximal end at which proximal body portion (62) terminates proximally, and a squared distal end defined by a spreading tip (68) at which distal body portion (64) terminates distally. Adhesive spreader (60) has a lateral width measured between opposed lateral sides (70), and a thickness measured between opposed working sides (72). Adhesive spreader (60) is symmetric about a first midplane (P1) that bisects the monolithic body along its lateral width, and is also symmetric about a second midplane (P2) that bisects the monolithic body along its thickness, where the first and second midplanes (P1, P2) intersect along a longitudinal axis (A) of adhesive spreader (60). Accordingly, adhesive spreader (60) may be used in various orientations interchangeably. Each of proximal body portion (62) and distal body portion (64) has a generally elongate oval-shaped cross-section that has a generally constant thickness through proximal body portion (62) and tapers in thickness distally through distal body portion (64) toward spreading tip (68), which defines a minimum thickness of adhesive spreader (60) and thus has a lesser rigidity than the proximal remainder of adhesive spreader (60). Accordingly, spreading tip (68) may be configured to elastically deflect before and at a faster rate than flexural body portion (66) when pressed against an application surface. Cross-sectional shapes and elastic deflection characteristics of spreading tip (68) and flexural body portion (66) are described in greater detail below.

Figure 5:
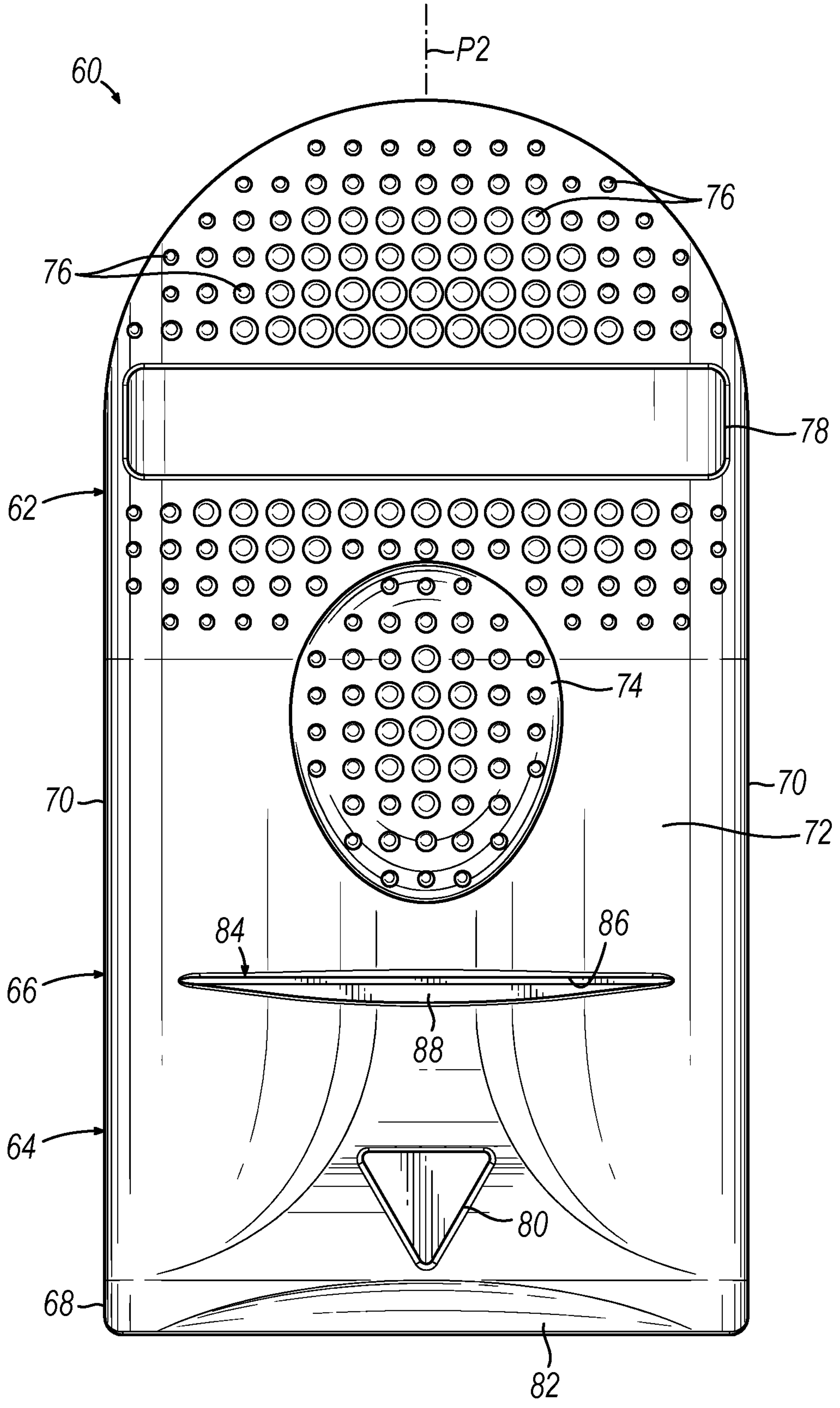
FIG. 5 depicts a top plan view of the adhesive spreader of FIG. 1.
Figure 6:
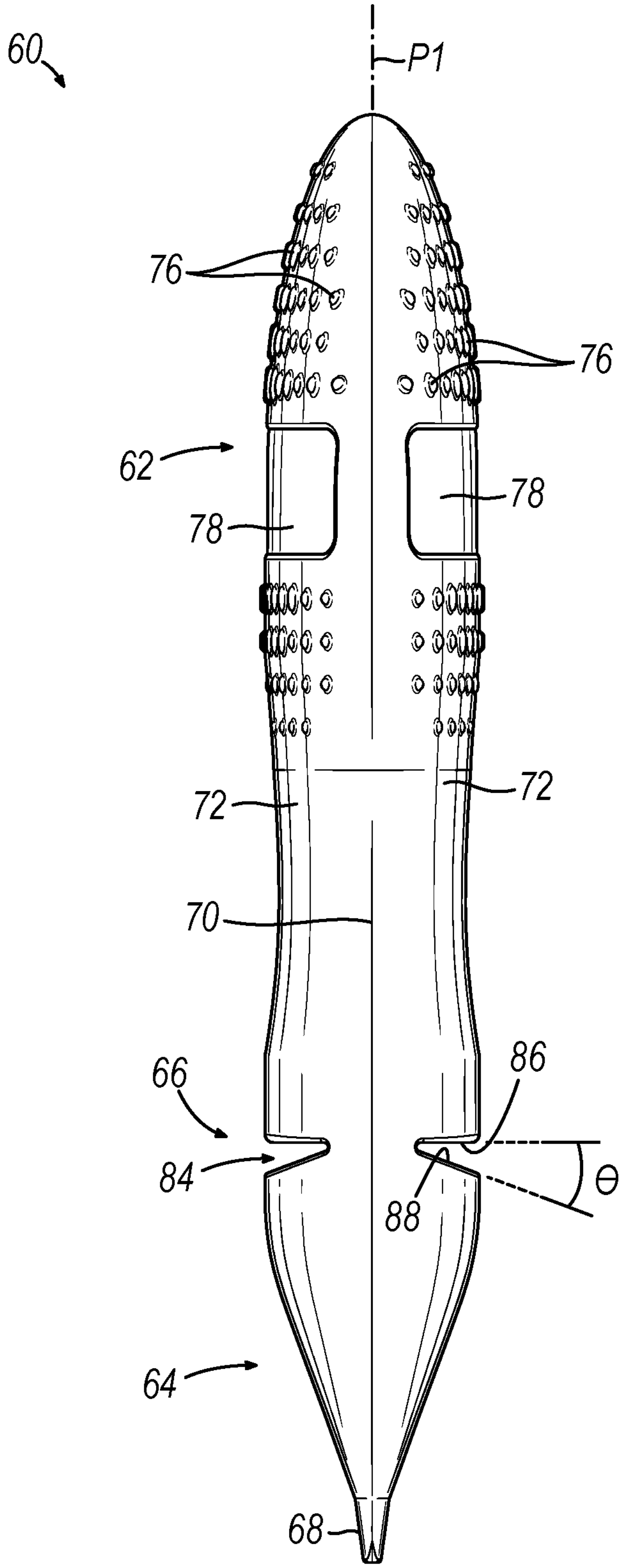
FIG. 6 depicts a side elevational view of the adhesive spreader of FIG. 1.

As shown in FIGS. 4-6, proximal body portion (62) on each working side (72) of adhesive spreader (60) includes a finger well (74) that is located just proximal to flexural body portion (66) and is recessed inwardly with a concave curvature. Each finger well (74) is sized and shaped to receive one or more fingers, such as a thumb, of a user to promote effective griping of proximal body portion (62). A plurality of surface gripping features in the form of raised nubs (76) are arranged on each working side (72) of proximal body portion (62) within finger wells (74) and on at least a proximal half of proximal body portion (62). Raised nubs (76) are configured to further promote effective gripping of proximal body portion (62) in the presence of fluids, such bodily fluids or saline, that might otherwise make proximal body portion (62) slippery during a surgical procedure, or when the user grasps proximal body portion (62) with gloved fingers. Proximal body portion (62) on each working side (72) also includes a recessed area (78) proximal to finger well (74) that may include visual indicia (not shown), such as product branding, though it will be appreciated that recessed areas (78) are merely optional.

As shown in FIGS. 4-6, distal body portion (64) tapers distally toward spreading tip (68) and includes on each working side (72) an alignment indicator (80) positioned along the longitudinal axis (A) of adhesive spreader (60). In the present version, each alignment indicator (80) is shown in the form of a triangular recess, though alignment indicators (80) may be of various other configurations may be employed in other versions. During use, adhesive spreader (60) is oriented relative to wound (W) and wound closure device (20) such that the distal tips of alignment indicators (80) are aligned with the longitudinal centerline of wound (W) and wound closure device (20), and this alignment is maintained as adhesive spreader (60) is pulled in a stroke longitudinally across wound closure device (20). As shown best in FIG. 5, spreading tip (68) extends transversely to the longitudinal axis (A) of adhesive spreader (60) and it includes a central planar surface (82) on each working side (72). Additionally, adhesive spreader (60) may be sized such that spreading tip (68) is slightly wider than wound closure device (20) so that spreading tip (68) may span the full width of wound closure device (20) and partially onto skin (S) on each side of wound closure device (20) during use. By way of example only, wound closure device (20) may be approximately 4 cm wide and adhesive spreader (60) may be approximately 4.5 cm wide, including at spreading tip (68).

Still referring to FIGS. 4-6, flexural body portion (66) on each working side (72) of adhesive spreader (60) includes a void feature shown in the form of a wedge-shaped channel (84). As used herein, "void" refers to an absence of material. Each wedge-shaped channel (84) is centered on the longitudinal axis (A) of adhesive spreader (60) and has a length that is equal to approximately 80% of the lateral width of adhesive spreader (60). As shown best in FIG. 6, each wedge-shaped channel (84) has a proximal surface (86) that is generally perpendicular to first midplane (P1), and a distal surface (88) that is obliquely angled relative to first midplane (P1). Proximal and distal surfaces (86, 88) of each wedge-shaped channel (84) define an outwardly opening angle (0) of approximately 20°.

Figures 7A, 7B:
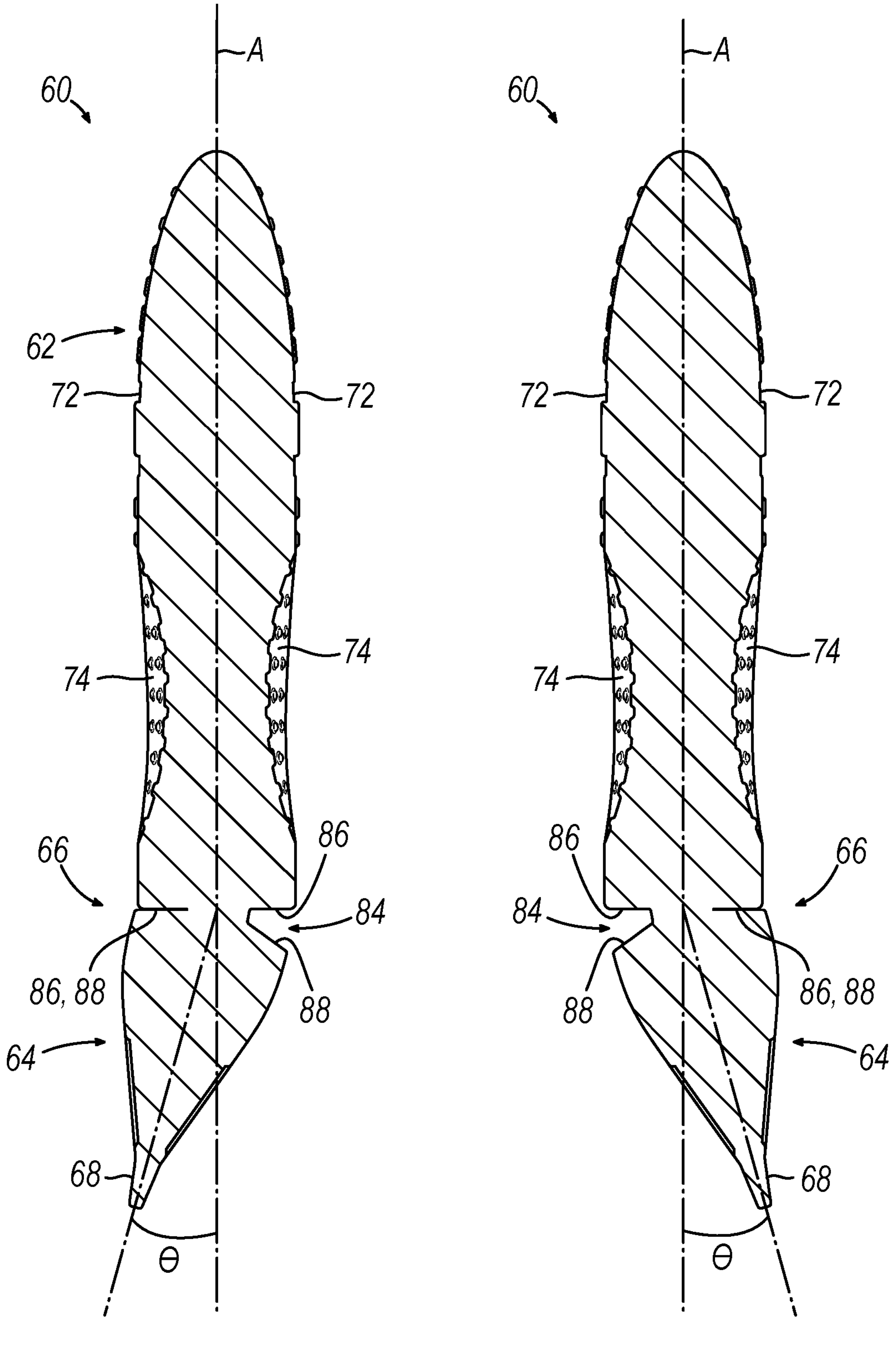
FIG. 7A depicts a side sectional view of the adhesive spreader of FIG. 1, taken along line 7-7 of FIG. 4, showing a distal body portion of the adhesive spreader deflected in a first direction.
FIG. 7B depicts a side sectional view of the adhesive spreader of FIG. 1, taken along line 7-7, showing the distal body portion deflected in a second direction.

As shown in FIGS. 7A-7B, wedge-shaped channels (84) cooperate to provide a central web portion of flexural body portion (66) with a lesser rigidity than proximal body portion (62) such that flexural body portion (66) is configured to elastically deform so that distal body portion (64) angularly deflects relative to proximal body portion (62) when spreading tip (68) is pressed against an application surface by a user. More specifically, in response to a user input force, distal body portion (64) is configured to pivotably hinge relative to proximal body portion (62) about a transverse hinge axis defined by flexural body portion (66) that extends along first midplane (P1) and orthogonally intersects second midplane (P2). Distal body portion (64) may deflect in a first direction by a maximum deflection angle (0) as shown in FIG. 7A, and also in an opposite second direction by maximum deflection angle (0) as shown in FIG. 7B. When distal body portion (64) assumes the maximum deflection angle (0) in either direction, proximal and distal surfaces (86, 88) of the wedge-shaped channel (84) in the direction of deflection contact one another and thus act as mechanical stops to inhibit further deflection of distal body portion (64) in that direction. When the user input force is released, for example when adhesive spreader (60) is lifted from an application surface, distal body portion (64) may resilient snap back to its relaxed state shown in FIG. 6 in which proximal and distal body portions (62, 64) extend coaxially along the longitudinal axis (A), centered about first midplane (P1).

During use of adhesive spreader (60), the user grips proximal body portion (62) and positions spreading tip (68) in contact with an application surface, such as mesh (22) of wound closure device (20) and/or skin (S). The user then leans adhesive spreader (60) so that its longitudinal axis (A) defined by proximal body portion (62) defines a lean angle relative to the application surface of approximately 45° to approximately 60°, as shown in FIGS. 3E-3F. The user then applies a downward force through proximal body portion (62) in a direction normal to the application surface while dragging adhesive spreader (60) across the application surface such that proximal body portion (62) leads distal body portion (64). Due to the lean angle, the applied force creates a moment about spreading tip (68) that may be sufficient to cause flexural body portion (66) to elastically deform, due to its reduced thickness, such that distal body portion (64) angularly deflects relative to proximal body portion (62) in a hinge-like manner. This elastic deformation of flexural body portion (66) may result in spreading tip (68) exerting a normal force against the application surface and the topical skin adhesive that is approximately 1.5 lbf to approximately 5 lbf when proximal body portion (62) is oriented within the lean angle range noted above.

As proximal body portion (62) is oriented at lean angles greater than 60°, then the moment generated at spreading tip (68) progressively decreases resulting in less deformation of flexural body portion (66) such that the user-applied force is transmitted more directly through spreading tip (68) to the application surface. For instance, if proximal body portion (62) is oriented at a lean angle of 90° such that proximal body portion (62) is perpendicular to the application surface, then spreading tip (68) may exert a normal force of up to approximately 10 lbf. It will be appreciated that greater normal forces may be required when spreading topical skin adhesives of greater viscosity such as a silicone-based adhesive like topical skin adhesive (54), to force topical skin adhesive (54) through wound closure device (20) and into contact with the underlying wound (W) and skin (S). Conversely, lesser normal forces may be required when spreading topical skin adhesives of lesser viscosity, which may pass through wound closure device (20) more easily. Accordingly, when adhesive spreader (60) is oriented in the illustrative lean angle range noted above, spreading of higher viscosity adhesives will result in greater deflection of flexural body portion (66), for example to the point that channel surfaces (86, 88) contact one another. Conversely, spreading of lower viscosity adhesives will result in lesser deflection or no deflection of flexural body portion (66).

The flexibility of flexural body portion (66) enables a user to employ enhanced control and precession when spreading topical skin adhesive (54) over wound closure device (20). In that regard, adhesive spreader (60) is configured to spread topical skin adhesive (54) effectively over and through wound closure device (20) with a suitable normal force that may fall within the predetermined range noted above, depending on the viscosity of topical skin adhesive (54) and how adhesive spreader (60) is manipulated by the user. Accordingly, flexural body portion (66) may operate to limit the normal force when spreading topical adhesives of relatively lower viscosity and may operate to ensure a predetermined minimum normal force when spreading topical skin adhesives of relatively higher viscosity. Moreover, the construction of adhesive spreader (60) enables it to apply the normal force consistently over wound closure device (20) to create a film of topical skin adhesive (54) having a uniform film thickness, such as approximately 0.5 mm. Adhesive spreader (60) may also facilitate creation of film edges with a tapered thickness that help minimize the risk of the cured adhesive catching onto the patient's clothing or other articles positioned against the patient's skin (S).

Figure 8:
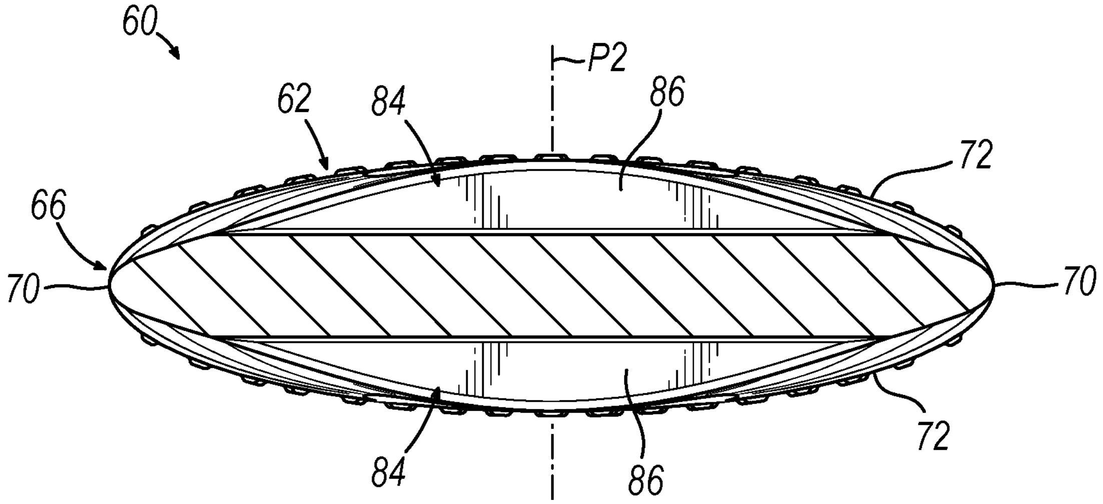
FIG. 8 depicts an end sectional view of the adhesive spreader of FIG. 1, taken along line 8-8 of FIG. 4.
Figure 9:
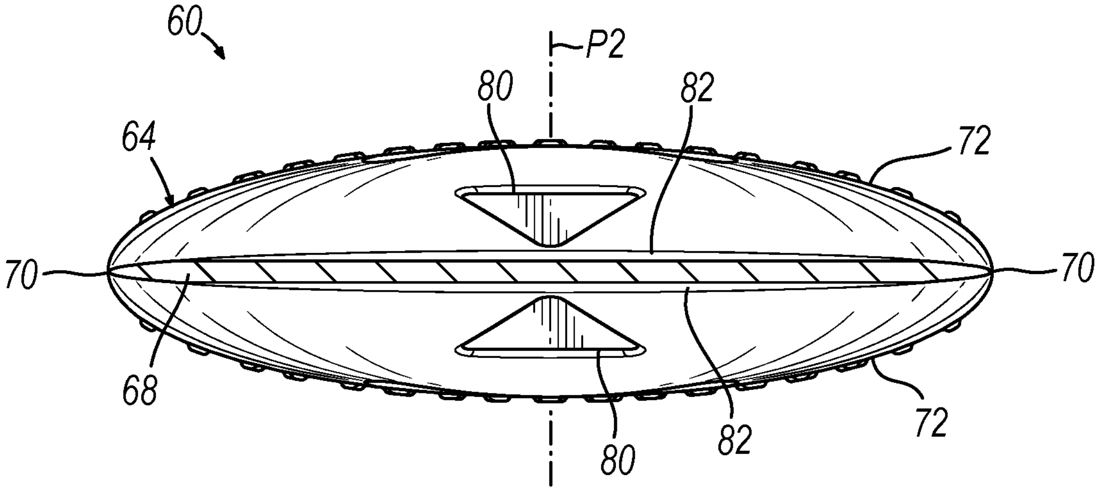
FIG. 9 depicts an end sectional view of the adhesive spreader of FIG. 1, taken along line 9-9 of FIG. 4.

As shown in FIGS. 8 and 9, each of flexural body portion (66) and spreading tip (68) has a non-uniform thickness, and thus a non-uniform rigidity and buckling strength, along the lateral width of adhesive spreader (60). More specifically, the thickness and buckling strength of flexural body portion (66) increases from the second midplane (P2) in orthogonal directions toward lateral sides (70), where a maximum thickness and buckling strength of flexural body portion (66) is defined at each longitudinal end of wedge-shaped channels (84) adjacent to lateral sides (70). Accordingly, flexural body portion (66) has a minimum rigidity and buckling strength along the second midplane (P2) and a maximum rigidity and buckling strength along lateral sides (70). Accordingly, these regions of maximum buckling strength along lateral sides (70) function as structural beam-like features.

Figure 10:
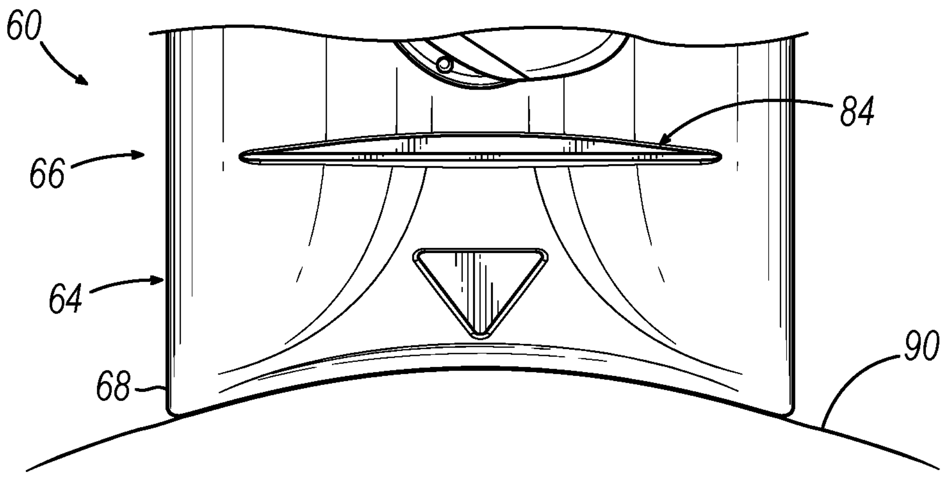
FIG. 10 depicts a plan view of the distal body portion of the adhesive spreader of FIG. 1, showing a spreading tip of the adhesive spreader conforming to a convexly curved skin surface.
Figure 11:
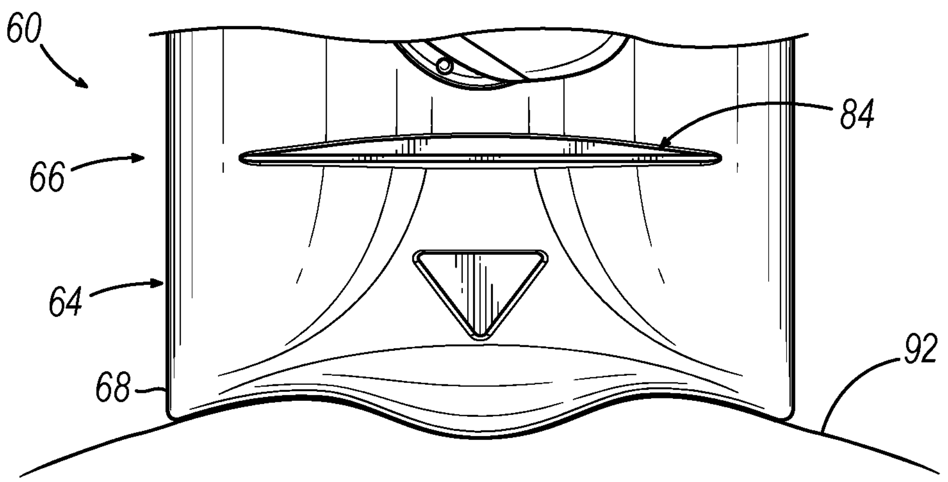
FIG. 11 depicts a plan view of the distal body portion of the adhesive spreader of FIG. 1, showing the spreading tip conforming to a convexly and concavely curved skin surface.

As shown in FIG. 9, spreading tip (68) exhibits an inverse configuration from flexural body portion (66) regarding thickness and buckling strength. More specifically, the thickness and buckling strength of spreading tip (68) decreases from the second midplane (P2) in orthogonal directions toward lateral sides (70), where a maximum thickness of flexural body portion (66) is defined at the second midplane (P2). Accordingly, spreading tip (68) has a maximum rigidity and buckling strength along the second midplane (P2) and a minimum rigidity and buckling strength along lateral sides (70). The inversely configured thicknesses and buckling strengths of flexural body portion (66) and spreading tip (68) enable adhesive spreader (60) to elastically deform axially along longitudinal axis (A) so that spreading tip (68) may conform to various types of contoured application surfaces. For instance, FIG. 10 shows spreading tip (68) conforming to a convex application surface (90) and FIG. 11 shows spreading tip (68) conforming to an undulating application surface (92) having both convex and concave portions. Such application surfaces (90, 92) may be representative of patient body joints such as a knee, wrist, or elbow, for example.

To exhibit the various functional characteristics described above, adhesive spreader (60) may be formed of an elastomeric material having a hardness of approximately 50 Shore A to approximately 70 Shore A, such as approximately 60 Shore A, where the elastomeric material is non-reactive with topical skin adhesive (54), wound closure device (20), and skin (S). By way of example only, adhesive spreader (60) may comprise a silicone rubber, and may be formed by injection molding. In other versions, two or more portions of adhesive spreader (60) may be formed of different materials, where at least flexural body portion (66) and spreading tip (68) are formed of elastomeric materials. Additionally, all or least a distal portion of adhesive spreader (60) may be at least at least partially transparent to enable visualization through adhesive spreader (60) while spreading a topical adhesive and promote alignment of alignment indicators (80) with the wound (W).

III. ALTERNATIVE ADHESIVE SPREADERS

In some instances, it may be desirable to provide an adhesive spreader that includes a flexural body portion having a void feature other than wedge-shaped channels (84), where the void feature provides the flexural body portion with a buckling strength that varies along a lateral width of the adhesive spreader, and where the void feature promotes elastic deformation of the flexural body portion to enable a distal body portion of the spreader to angularly deflect relative to a proximal body portion to regulate a normal force applied by the spreader to the application surface. FIGS. 12-16 show illustrative alternative adhesive spreaders (100, 120) configured in such a manner, where adhesive spreaders (100, 120) are similar to adhesive spreader (60) except as otherwise described below.

Figure 12:
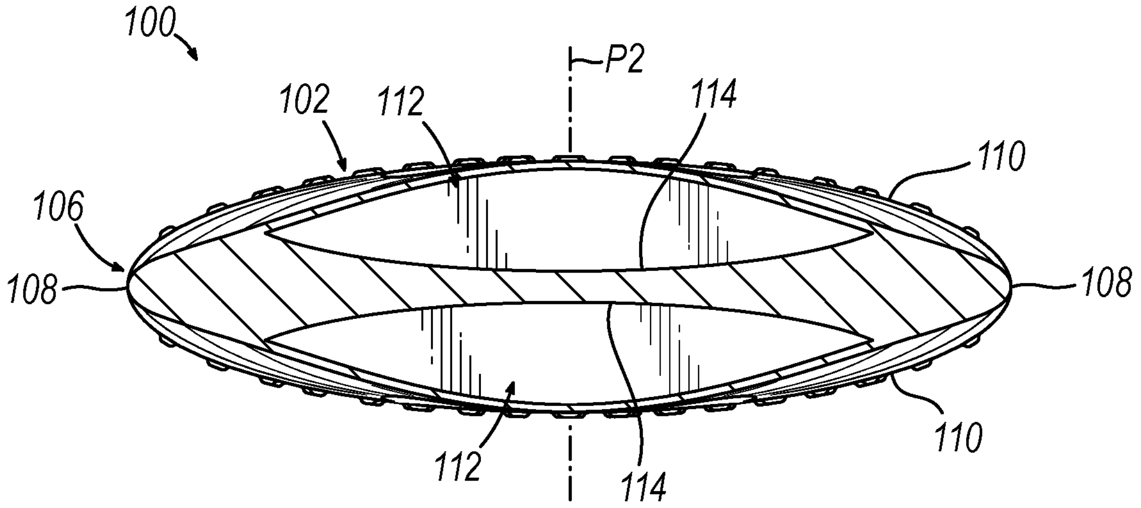
FIG. 12 depicts an end sectional view of another illustrative adhesive spreader configured for use with the wound closure system of FIG. 1.

FIG. 12 shows an alternative adhesive spreader (100) that includes a proximal body portion (102) similar to proximal body portion (62), a distal body portion (not shown) similar to distal body portion (64), a unique flexural body portion (106), a pair of lateral sides (108), and a pair of working sides (110). Flexural body portion (106) includes a void feature in the form of a pair of wedge-shaped channels (112) that are opposed from one another about first midplane (P1) (see FIGS. 4 and 6). Each channel (112) has a root (114) that extends concavely relative to first midplane (P1). Accordingly, similar to flexural body portion (66), a thickness and buckling strength of flexural body portion (106) increases from second midplane (P2) in orthogonal directions toward lateral sides (108). In particular, flexural body portion (106) has a minimum thickness and buckling strength along second midplane (P2), and a maximum thickness and buckling strength at the lateral ends of wedge-shaped channels (112) adjacent to lateral sides (108).

Figure 13:
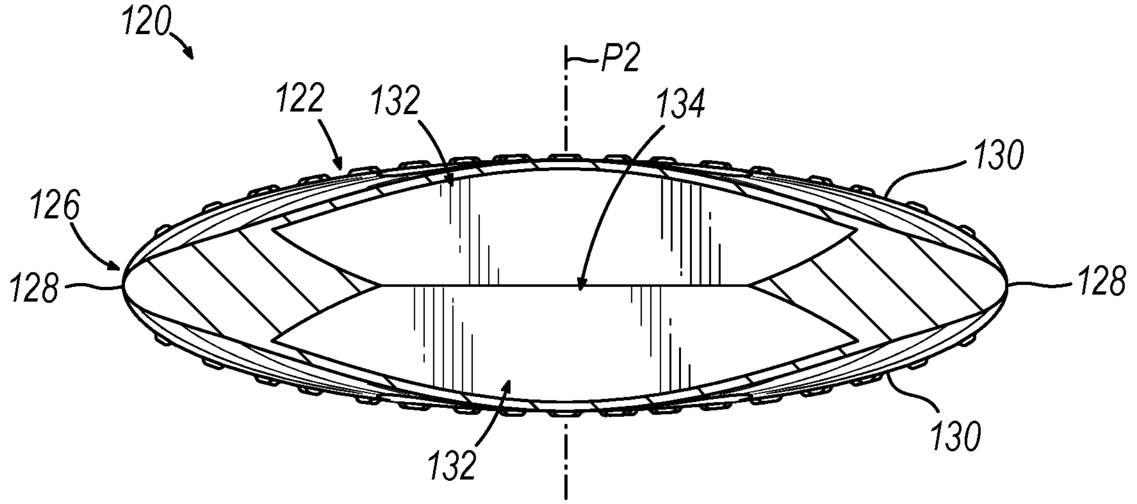
FIG. 13 depicts an end sectional view of another illustrative adhesive spreader configured for use with the wound closure system of FIG. 1.

FIG. 13 shows another alternative adhesive spreader (120) that includes a proximal body portion (122) similar to proximal body portion (62), a distal body portion (not shown) similar to distal body portion (64), a unique flexural body portion (126), a pair of lateral sides (128), and a pair of working sides (130). Flexural body portion (126) includes a void feature in the form of a pair of wedge-shaped openings (132) that are opposed from one another about first midplane (P1) (see FIGS. 4 and 6). Wedge-shaped openings (132) are similar to wedge-shaped channels (84, 112) but communicate with one another to define a central opening (134) (also referred to as a window) that extends fully through the central portion of flexural body portion (126) and longitudinally along first midplane (P1), such that central opening (134) opens to each working side (130). Similar to flexural body portions (66, 106), a thickness and buckling strength of flexural body portion (106) increases in a direction away from second midplane (P2) toward lateral sides (128). In particular, flexural body portion (126) has a minimum buckling strength at second midplane (P2) and along the length of central opening (124), and a maximum buckling strength at the lateral ends of wedge-shaped openings (132).

Figure 14:
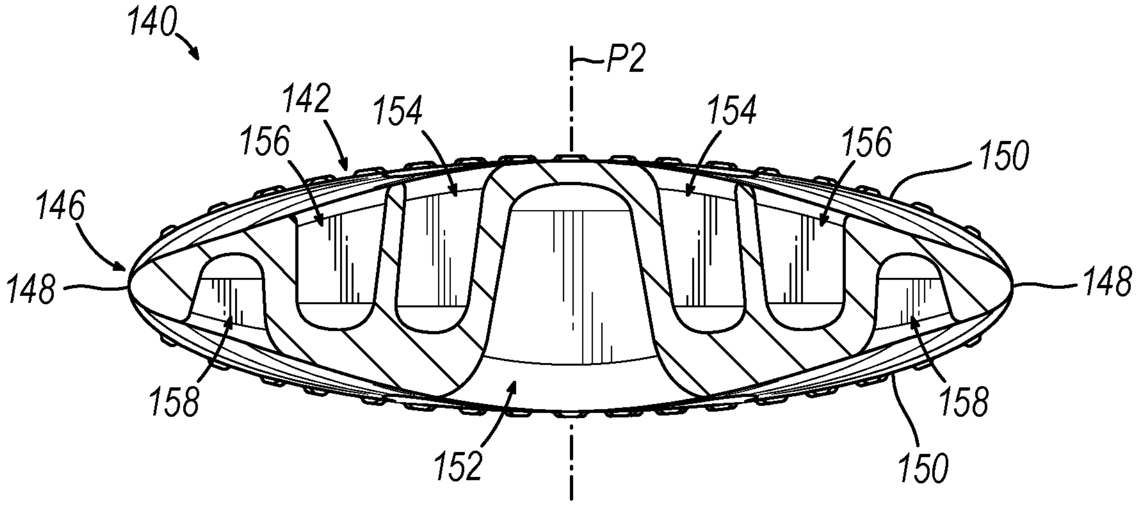
FIG. 14 depicts an end sectional view of another illustrative adhesive spreader configured for use with the wound closure system of FIG. 1.

FIG. 14 shows another alternative adhesive spreader (140) that includes a proximal body portion (142) similar to proximal body portion (62), a distal body portion (not shown) similar to distal body portion (64), a unique flexural body portion (146), a pair of lateral sides (148), and a pair of working sides (150). Flexural body portion (146) includes a void feature in the form a plurality of recesses (152, 154, 156, 158) formed in working sides (150), where recesses (152, 154, 156, 158) are arranged symmetrically about second midplane (P2) and are separated from one another by a respective web of material. In particular, a central recess (152) is centered laterally on second midplane (P2) and opens through the second working side (150) and is closed along the first working side (150). A first intermediate recess (154) is disposed on each lateral side of central recess (152) and opens through the first working side (150) and is closed along the second working side (150). A second intermediate recess (156) is disposed laterally outwardly of each first intermediate recess (154) and likewise opens through the second working side (150) and is closed along the first working side (150). Finally, an outer recess (158) is disposed laterally outwardly of each second intermediate recess (156), adjacent to each lateral side (148), where each outer recess (158) opens through the second working side (150) and is closed along the first working side (150), similar to central recess (152).

In the present version, an internal volume of recesses (152, 154, 156, 158) decreases in a direction away from second midplane (P2), where central recess (152) has the greatest internal volume of recesses (152, 154, 156, 158) and each outer recess (158) has a minimum internal volume of recesses (152, 154, 156, 158). Additionally, the web of material that separates outer recesses (158) from second intermediate recesses (156) is thicker than the web of material that separates first and second intermediate recesses (154 156). Accordingly, the buckling strength of flexural body portion (146) increases in a direction away from second midplane (P2), with a minimum buckling strength at second midplane (P2) and a maximum buckling strength at lateral sides (148).

Figure 15:
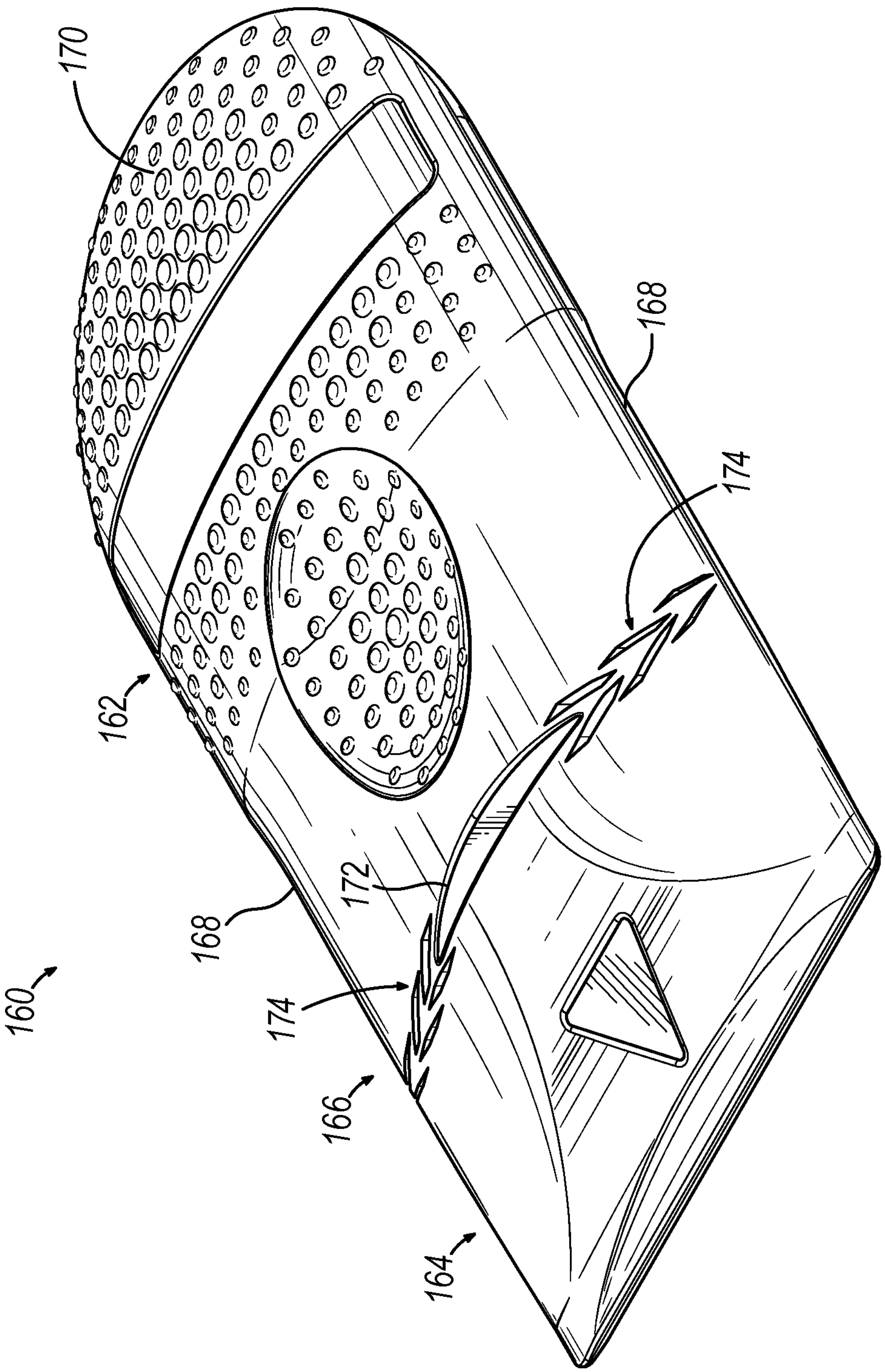
FIG. 15 depicts a perspective view of another illustrative adhesive spreader configured for use with the wound closure system of FIG. 1.

FIG. 15 shows another alternative adhesive spreader (160) that includes a proximal body portion (162) similar to proximal body portion (62), a distal body portion (164) similar to distal body portion (64), a unique flexural body portion (166), a pair of lateral sides (168), and a pair of working sides (170). Flexural body portion (166) of the present example includes a first void feature in the form of a pair of wedge-shaped channels (172), and a second void feature in the form of an array of angled slits (174) that are formed between the lateral ends of wedge-shaped channels (172) and the lateral sides (168) of adhesive spreader (160). Angled slits (174) extend fully through the thickness of adhesive spreader (160) and are arranged in pairs, where each pair defines an arrow or chevron-like shape having an apex oriented toward a respective lateral side (168). Additionally, angled slits (174) have a progressively larger opening size in a direction advancing from the lateral sides (168) toward the second midplane (P2) that bisects adhesive spreader (160) along its thickness. Accordingly, a buckling strength of flexural body portion (166) decreases in a direction toward the second midplane (P2) from lateral sides (168).

Figure 16:
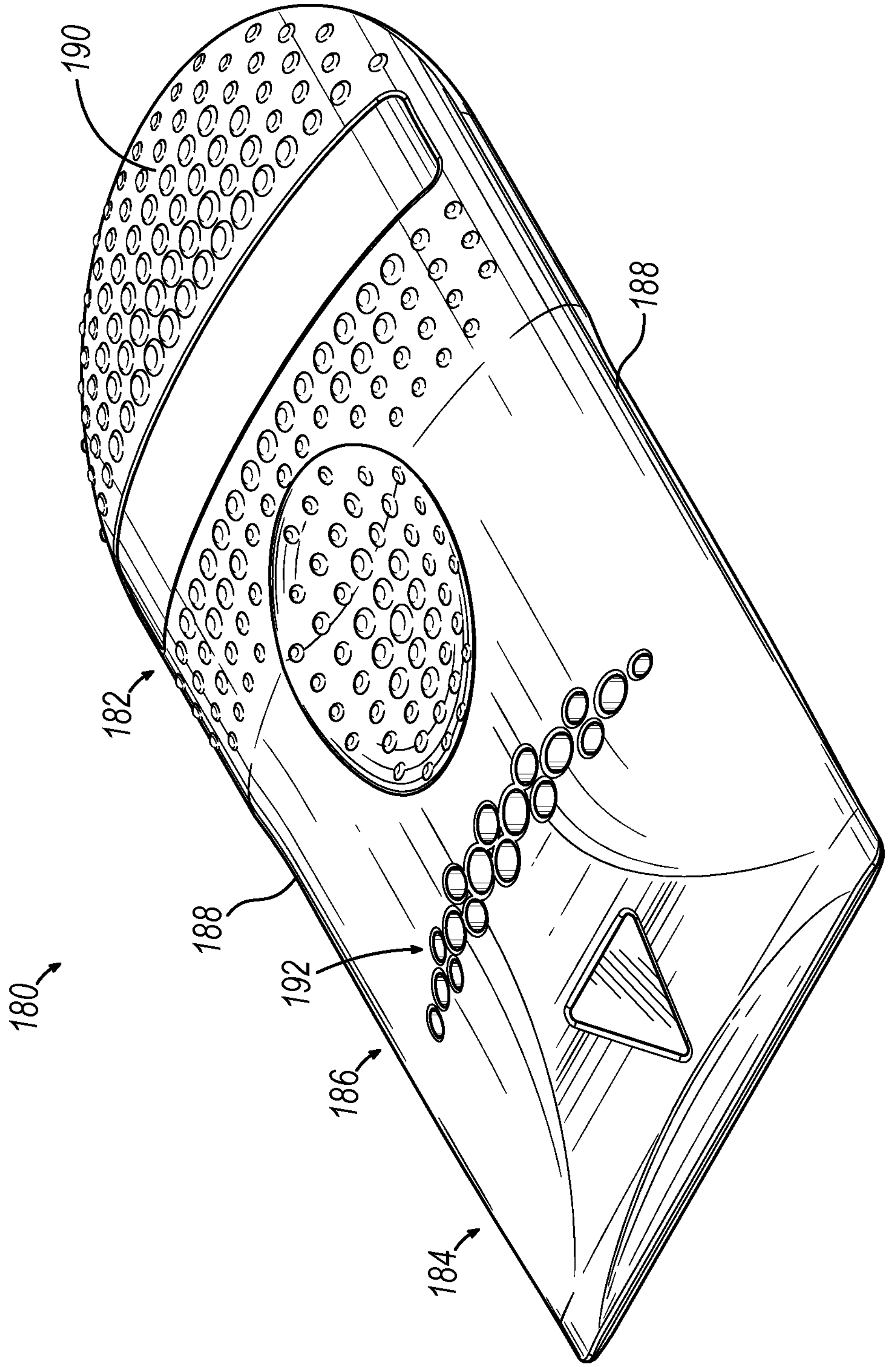
FIG. 16 depicts a perspective view of another illustrative adhesive spreader configured for use with the wound closure system of FIG. 1.

FIG. 16 shows another alternative adhesive spreader (180) that includes a proximal body portion (182) similar to proximal body portion (62), a distal body portion (184) similar to distal body portion (64), a unique flexural body portion (186), a pair of lateral sides (188), and a pair of working sides (190). Flexural body portion (186) of the present example includes a void feature in the form of an array of bores (192) that extend fully through the thickness of adhesive spreader (180) along a linear path that extends transversely to the longitudinal axis of adhesive spreader (180) and parallel to the second midplane (P2). In the present version, bores (192) are formed symmetrically about the second midplane (P2), and the average diameter and density of bores (192) increases in a direction toward the second midplane (P2). Accordingly, a buckling strength of flexural body portion (186) decreases in a direction toward the second midplane (P2).

IV. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a proximal body portion configured to be gripped by a user; (b) a distal body portion that terminates distally at a spreading tip configured to spread a topical skin adhesive along an application surface; and (c) a flexural body portion that interconnects the proximal and distal body portions to define a monolithic body, wherein in response to an input force applied by a user to the proximal body portion when the spreading tip is positioned against the application surface, the flexural body portion is configured to at least one of: (i) buckle non-uniformly along a lateral width of the apparatus, or (ii) elastically deform so that the distal body portion angularly deflects relative to the proximal body portion to thereby limit to a predetermined range a resultant normal force exerted by the spreading tip on the topical skin adhesive along the application surface.

Example 2

The apparatus of Example 1, wherein the monolithic body comprises an elastomeric material having a hardness of approximately 50 Shore A to approximately 70 Shore A.

Example 3

The apparatus of Example any of the preceding Examples, wherein the elastomeric material comprises a silicone rubber.

Example 4

The apparatus of any of the preceding Examples, wherein the proximal body portion extends along a longitudinal axis, wherein the spreading tip is configured to exert a normal force on the topical skin adhesive of approximately 1.5 lbf to approximately 5 lbf when the flexural body portion is in an elastically deformed state such that the distal body portion is angularly deflected relative to the proximal body portion.

Example 5

The apparatus of any of the preceding Examples, wherein the flexural body portion includes a void feature.

Example 6

The apparatus of Example 5, wherein the void feature includes a pair of wedge-shaped channels arranged on opposing sides of the monolithic body, wherein each of the wedge-shaped channels extends transversely to a longitudinal axis of the apparatus.

Example 7

The apparatus of Example 6, wherein each of the wedge-shaped channels has first and second opposed surfaces that define an angle of approximately 20°.

Example 8

The apparatus of any of the preceding Examples, wherein the distal body portion tapers distally and the spreading tip defines a minimum thickness of the monolithic body.

Example 9

The apparatus of any of the preceding Examples, wherein each of the flexural body portion and the spreading tip has a non-uniform thickness along a lateral width of the monolithic body such that a buckling strength of the flexural body portion varies along the lateral width.

Example 10

The apparatus of any of the preceding Examples, wherein the monolithic body is symmetric about a midplane that bisects the monolithic body between opposed lateral sides of the monolithic body.

Example 11

The apparatus of Example 10, wherein a buckling strength of the flexural body portion increases from the midplane in orthogonal directions toward the lateral sides, wherein a buckling strength of the spreading tip decreases from the midplane in orthogonal directions toward the lateral sides.

Example 12

The apparatus of any of the preceding Examples, wherein a thickness of the flexural body portion increases from the midplane in orthogonal directions toward the lateral sides, wherein a thickness of the spreading tip decreases from the midplane in orthogonal directions toward the lateral sides.

Example 13

The apparatus of any of the preceding Examples, wherein distal body portion is at least partially transparent and includes an alignment indicator configured to be aligned with a longitudinal axis of a wound when spreading topical adhesive over the wound.

Example 14

A system comprising: (a) a wound closure device having a mesh layer and a pressure sensitive adhesive layer on an underside of the mesh layer, wherein the wound closure device is configured to be applied over a wound in a patient's skin; (b) an adhesive applicator containing a topical skin adhesive, wherein the adhesive applicator is operable to dispense the topical skin adhesive onto the mesh layer of the applied wound closure device; and (c) the apparatus of Example 1, wherein the apparatus is configured to spread topical skin adhesive applied to the mesh layer of the wound closure device by the adhesive applicator.

Example 15

The system of Example 14, wherein the topical skin adhesive comprises silicone.

Example 16

An apparatus, comprising: (a) a proximal body portion; (b) a distal body portion that extends coaxially with the proximal body portion and terminates distally at a spreading tip configured to spread a topical skin adhesive along an application surface; and (c) a flexural body portion that interconnects the proximal and distal body portions to define a monolithic body, wherein the flexural body portion includes a void feature configured to promote elastic deformation of the monolithic body at the flexural body portion so that the distal body portion angularly deflects relative to the proximal body portion in response to an input force applied by a user to the proximal body portion to thereby limit a resultant normal force exerted by the spreading tip on the topical skin adhesive along the application surface.

Example 17

The apparatus of Example 16, wherein the void feature comprises a pair of wedge-shaped channels arranged on opposing sides of the monolithic body.

Example 18

The apparatus of any of Examples 16 through 17, wherein the flexural body portion has a buckling strength that varies along a lateral width of the monolithic body, wherein the flexural body portion has a minimum buckling strength at its lateral mid-point.

Example 19

An apparatus, comprising: (a) a proximal body portion configured to be gripped by a user; (b) a distal body portion that terminates distally at a spreading tip configured to spread a topical skin adhesive along an application surface; and (c) a flexural body portion that interconnects the proximal and distal body portions to define a monolithic body, wherein the flexural body portion is configured to elastically deform so that the distal body portion angularly deflects relative to the proximal body portion in response to an input force applied by a user to the proximal body portion to thereby limit a resultant normal force exerted by the spreading tip on the topical skin adhesive along the application surface, wherein the monolithic body is symmetric about a midplane that bisects the monolithic body along its thickness between opposed lateral sides of the monolithic body, wherein a thickness of the flexural body increases or decreases from the midplane in orthogonal directions toward the lateral sides, wherein a thickness of the spreading tip the other of increases or decreases from the midplane in orthogonal directions toward the lateral sides.

Example 20

The apparatus of Example 19, wherein the thickness of the flexural body portion increases from the midplane in directions toward the lateral sides, wherein the thickness of the spreading tip decreases from the midplane in orthogonal directions toward the lateral sides.

Example 21

A system, comprising: (a) a wound closure device having a mesh layer and a pressure sensitive adhesive layer on an underside of the mesh layer, wherein the wound closure device is configured to be applied over a wound in a patient's skin; (b) an adhesive applicator containing a topical skin adhesive, wherein the adhesive applicator is operable to dispense the topical skin adhesive onto the mesh layer of the applied wound closure device; and (c) an adhesive spreader operable to spread the applied topical skin adhesive over and through the wound closure device, wherein the adhesive spreader comprises: (i) a proximal body portion configured to be gripped by a user, (ii) a distal body portion that terminates distally at a spreading tip configured to spread the topical skin adhesive along a top surface of the wound closure device, and (iii) a flexural body portion that interconnects the proximal and distal body portions to define a monolithic body, wherein in response to an input force applied by a user to the proximal body portion when the spreading tip is positioned against the application surface, the flexural body portion is configured to elastically deform so that the distal body portion angularly deflects relative to the proximal body portion to thereby limit to a predetermined range a resultant normal force exerted by the spreading tip on the topical skin adhesive along the top surface.

Example 22

The apparatus of Example 21, wherein the topical skin adhesive is curable and is configured to remain elastomeric after curing.

Example 23

The apparatus of Example 22, wherein the topical skin adhesive comprises silicone.

Example 24

A method of spreading a topical skin adhesive on a wound closure device positioned over a wound in the skin of a patient with an adhesive spreader that includes a proximal body portion, a distal body portion that terminates distally at a spreading tip, and a flexural body portion that interconnects the proximal and distal body portions, the method comprising: (a) positioning the spreading tip in contact with the topical skin adhesive on a top surface of the wound closure device; (b) angling the adhesive spreader such that its longitudinal axis defines an angle of approximately 45° to approximately 60° relative to the top surface; (c) applying a force to the proximal body portion such that the flexural body portion elastically deforms and the distal body portion angularly deflects relative to the proximal body portion such that the spreading tip exerts a normal force on the topical skin adhesive and the top surface in the range of approximately 1.5 lbf to approximately 5 lbf; and (d) dragging the spreading tip along the top surface to force the topical skin adhesive through the wound closure device.

Example 25

The apparatus of Example 24, wherein the topical skin adhesive comprises silicone.

V. MISCELLANEOUS

It is understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 29/860,717, entitled "Device for Spreading Topical Skin Adhesive," filed Nov. 22, 2022, issued as U.S. Pat. No. D1,073,065 on Apr. 29, 2025, the disclosure of which is incorporated by reference herein, in its entirety; U.S. patent application Ser. No. 17/991,992, entitled "Application of Topical Skin Adhesive to Surgical Mesh," filed Nov. 22, 2022, published as U.S. Pub. No. 2024/0165292 on May 23, 2024, the disclosure of which is incorporated by reference herein, in its entirety; U.S. patent application Ser. No. 17/991,945, entitled "Surgical Mesh Securing Device for Wound Closure System," filed Nov. 22, 2022, published as U.S. Pub. No. 2024/0164777 on May 23, 2024, the disclosure of which is incorporated by reference herein, in its entirety; and/or U.S. patent application Ser. No. 17/991,950, entitled "Wound Closure System Having Microcannulaic Pathways," filed Nov. 22, 2022, published as U.S. Pub. No. 2024/0164950 on May 23, 2024, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

(a) a proximal body portion configured to be gripped by a user;

(b) a distal body portion that terminates distally at a spreading tip configured to spread a topical skin adhesive along an application surface; and (c) a flexural body portion that interconnects the proximal and distal body portions to define a monolithic body having opposed lateral sides and being symmetric about a midplane that bisects the monolithic body between the lateral sides, wherein a buckling strength of the flexural body portion increases in a first direction between the midplane and each lateral side, and a buckling strength of the spreading tip increases in a second direction opposite the first direction between the midplane and each lateral side, wherein in response to an input force applied by a user to the proximal body portion when the spreading tip is positioned against the application surface, the flexural body portion is configured to:

(i) buckle non-uniformly along a lateral width of the monolithic body, and (ii) elastically deform so that the distal body portion angularly deflects relative to the proximal body portion to thereby limit a resultant normal force exerted by the spreading tip on the topical skin adhesive along the application surface.

2. The apparatus of claim 1, wherein the monolithic body comprises an elastomeric material having a hardness of approximately 50 Shore A to approximately 70 Shore A.

3. The apparatus of claim 2, wherein the elastomeric material comprises a silicone rubber.

4. The apparatus of claim 1, wherein the proximal body portion extends along a longitudinal axis, wherein the spreading tip is configured to exert a normal force on the topical skin adhesive of approximately 1.5 lbf to approximately 5 lbf when the flexural body portion is in an elastically deformed state such that the distal body portion is angularly deflected relative to the proximal body portion.

5. The apparatus of claim 1, wherein the flexural body portion includes at least one void.

6. The apparatus of claim 5, wherein the at least one void includes a pair of wedge-shaped channels arranged on opposing sides of the monolithic body, wherein each of the wedge-shaped channels extends transversely to a longitudinal axis of the apparatus.

7. The apparatus of claim 6, wherein each of the wedge-shaped channels has first and second opposed surfaces that define an angle of approximately 20°.

8. The apparatus of claim 1, wherein the distal body portion tapers distally and the spreading tip defines a minimum thickness of the monolithic body.

9. The apparatus of claim 1, wherein each of the flexural body portion and the spreading tip has a non-uniform thickness along the lateral width of the monolithic body such that the buckling strength of the flexural body portion varies along the lateral width.

10. The apparatus of claim 1, wherein the buckling strength of the flexural body portion increases from the midplane in orthogonal directions toward the lateral sides, wherein the buckling strength of the spreading tip decreases from the midplane in orthogonal directions toward the lateral sides.

11. The apparatus of claim 1, wherein a thickness of the flexural body portion increases from the midplane in orthogonal directions toward the lateral sides, wherein a thickness of the spreading tip decreases from the midplane in orthogonal directions toward the lateral sides.

12. The apparatus of claim 1, wherein the distal body portion is at least partially transparent and includes an alignment indicator configured to be aligned with a longitudinal axis of a wound when spreading topical adhesive over the wound.

13. A system comprising:

(a) a wound closure device having a mesh layer and a pressure sensitive adhesive layer on an underside of the mesh layer, wherein the wound closure device is configured to be applied over a wound in a patient's skin;

(b) an adhesive applicator containing a topical skin adhesive, wherein the adhesive applicator is operable to dispense the topical skin adhesive onto the mesh layer of the applied wound closure device; and (c) the apparatus of claim 1, wherein the apparatus is configured to spread topical skin adhesive applied to the mesh layer of the wound closure device by the adhesive applicator.

14. The system of claim 13, wherein the topical skin adhesive comprises silicone.

15. An apparatus, comprising:

(a) a proximal body portion;

(b) a distal body portion that extends coaxially with the proximal body portion and terminates distally at a spreading tip configured to spread a topical skin adhesive along an application surface; and (c) a flexural body portion that interconnects the proximal and distal body portions to define a monolithic body, wherein the flexural body portion includes at least one void configured to promote elastic deformation of the monolithic body at the flexural body portion so that the distal body portion angularly deflects relative to the proximal body portion in response to an input force applied by a user to the proximal body portion to thereby limit a resultant normal force exerted by the spreading tip on the topical skin adhesive along the application surface, wherein the at least one void extends along a lateral width of the flexural body portion so as to provide the flexural body portion with a buckling strength that varies along the lateral width and defines a minimum at a lateral mid-point of the flexural body portion.

16. The apparatus of claim 15, wherein the at least one void comprises a pair of wedge-shaped channels arranged on opposing sides of the monolithic body.

17. An apparatus, comprising:

(a) a proximal body portion configured to be gripped by a user;

(b) a distal body portion that terminates distally at a spreading tip configured to spread a topical skin adhesive along an application surface; and (c) a flexural body portion that interconnects the proximal and distal body portions to define a monolithic body, wherein the flexural body portion is configured to elastically deform so that the distal body portion angularly deflects relative to the proximal body portion in response to an input force applied by a user to the proximal body portion to thereby limit a resultant normal force exerted by the spreading tip on the topical skin adhesive along the application surface, wherein the monolithic body is symmetric about a midplane that bisects the monolithic body along its thickness between opposed lateral sides of the monolithic body, wherein a thickness of the flexural body portion increases or decreases from the midplane in orthogonal directions toward the lateral sides, wherein a thickness of the spreading tip the other of increases or decreases from the midplane in orthogonal directions toward the lateral sides.

18. The apparatus of claim 17, wherein the thickness of the flexural body portion increases from the midplane in directions toward the lateral sides, wherein the thickness of the spreading tip decreases from the midplane in orthogonal directions toward the lateral sides.

* * * * *